(12) United States Patent
Stinson

(10) Patent No.: US 8,002,821 B2
(45) Date of Patent: Aug. 23, 2011

(54) BIOERODIBLE METALLIC ENDOPROSTHESES

(75) Inventor: Jonathan S. Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 31 days.

(21) Appl. No.: 11/854,991

(22) Filed: Sep. 13, 2007

(65) Prior Publication Data

US 2008/0071350 A1    Mar. 20, 2008

Related U.S. Application Data

(60) Provisional application No. 60/845,341, filed on Sep. 18, 2006.

(51) Int. Cl.
*A61F 2/06* (2006.01)
(52) U.S. Cl. ............... 623/1.38; 623/1.44; 623/1.46
(58) Field of Classification Search .......... 623/1.38, 623/1.42, 1.44, 1.16, 1.43, 1.45, 1.46
See application file for complete search history.

(56) References Cited

U.S. PATENT DOCUMENTS

| | | | |
|---|---|---|---|
| 2,950,187 A | 8/1960 | Ototani |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |

(Continued)

FOREIGN PATENT DOCUMENTS

AU      739 507       11/1998

(Continued)

OTHER PUBLICATIONS

Kutsenko et al., "Structural changes in Mg alloy induced by plasma immersion ion implantation of Ag," *Acta Materialia*, 2004, 52:4329-4335.

(Continued)

*Primary Examiner* — David Isabella
*Assistant Examiner* — Andrew Iwamaye
(74) *Attorney, Agent, or Firm* — Fish & Richardson P.C.

(57) ABSTRACT

Endoprostheses such as stents are disclosed that are, or that include portions that are, bioerodible.

8 Claims, 7 Drawing Sheets

U.S. PATENT DOCUMENTS

| | | |
|---|---|---|
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,672,242 A | 9/1997 | Jen |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,761,775 A | 6/1998 | Legome et al. |
| 5,769,883 A | 6/1998 | Buscemi et al. |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,907,893 A | 6/1999 | Zadno-Azizi et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |

| | | | |
|---|---|---|---|
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,056,776 A | 5/2000 | Lau et al. |
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,240,616 B1 | 6/2001 | Yan |
| 6,241,762 B1 | 6/2001 | Shanley |
| 6,245,103 B1 | 6/2001 | Stinson |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz et al. |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,409,754 B1 | 3/2002 | Smith et al. |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,382 B1 | 4/2002 | Yang et al. |
| 6,379,383 B1 | 4/2002 | Palmaz et al. |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,447,540 B1 | 9/2002 | Fontaine et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |

| | | | | | | |
|---|---|---|---|---|---|---|
| 6,613,077 B2 | 9/2003 | Gilligan et al. | | 6,846,323 B2 | 1/2005 | Yip et al. |
| 6,613,083 B2 | 9/2003 | Alt | | 6,846,841 B2 | 1/2005 | Hunter et al. |
| 6,613,432 B2 | 9/2003 | Zamora et al. | | 6,847,837 B1 | 1/2005 | Melzer et al. |
| 6,616,765 B1 | 9/2003 | Castro et al. | | 6,849,085 B2 | 2/2005 | Marton |
| 6,626,933 B1 | 9/2003 | Lau et al. | | 6,849,089 B2 | 2/2005 | Stoll |
| 6,626,936 B2 | 9/2003 | Stinson | | 6,852,122 B2 | 2/2005 | Rush |
| 6,626,939 B1 | 9/2003 | Burnside et al. | | 6,854,172 B2 | 2/2005 | Kaese |
| 6,627,321 B1 | 9/2003 | Ellingsen et al. | | 6,861,088 B2 | 3/2005 | Weber et al. |
| 6,628,989 B1 | 9/2003 | Penner | | 6,865,810 B2 | 3/2005 | Stinson |
| 6,629,992 B2 | 10/2003 | Bigus et al. | | 6,866,805 B2 | 3/2005 | Hong et al. |
| 6,635,082 B1 | 10/2003 | Hossainy et al. | | 6,869,443 B2 | 3/2005 | Buscemi et al. |
| 6,638,302 B1 | 10/2003 | Curcio et al. | | 6,869,701 B1 | 3/2005 | Aita et al. |
| 6,641,607 B1 | 11/2003 | Hossainy et al. | | 6,875,227 B2 | 4/2005 | Yoon |
| 6,652,575 B2 | 11/2003 | Wang | | 6,878,249 B2 | 4/2005 | Kouyama et al. |
| 6,652,578 B2 | 11/2003 | Bailey et al. | | 6,884,429 B2 | 4/2005 | Koziak et al. |
| 6,652,581 B1 | 11/2003 | Ding | | 6,887,270 B2 | 5/2005 | Miller et al. |
| 6,652,582 B1 | 11/2003 | Stinson | | 6,887,857 B2 | 5/2005 | Naimark et al. |
| 6,660,034 B1 | 12/2003 | Mandrusov et al. | | 6,896,697 B1 | 5/2005 | Yip et al. |
| 6,663,662 B2 | 12/2003 | Pacetti et al. | | 6,899,731 B2 | 5/2005 | Li et al. |
| 6,663,664 B1 | 12/2003 | Pacetti | | 6,899,914 B2 | 5/2005 | Schaldach et al. |
| 6,669,980 B2 | 12/2003 | Hansen | | 6,904,658 B2 | 6/2005 | Hines |
| 6,673,105 B1 | 1/2004 | Chen | | 6,908,506 B2 | 6/2005 | Zimmermann |
| 6,673,385 B1 | 1/2004 | Ding et al. | | 6,908,622 B2 | 6/2005 | Barry et al. |
| 6,673,999 B1 | 1/2004 | Wang et al. | | 6,908,624 B2 | 6/2005 | Hossainy et al. |
| 6,676,987 B2 | 1/2004 | Zhong | | 6,913,617 B1 | 7/2005 | Reiss |
| 6,676,989 B2 | 1/2004 | Kirkpatrick et al. | | 6,913,765 B2 | 7/2005 | Li et al. |
| 6,689,160 B1 | 2/2004 | Okuda et al. | | 6,918,869 B2 | 7/2005 | Shaw et al. |
| 6,689,803 B2 | 2/2004 | Hunter | | 6,918,927 B2 | 7/2005 | Bates et al. |
| 6,695,865 B2 | 2/2004 | Boyle et al. | | 6,921,390 B2 | 7/2005 | Bucay-Couto et al. |
| 6,699,281 B2 | 3/2004 | Vallana et al. | | 6,923,996 B2 | 8/2005 | Epstein et al. |
| 6,699,282 B1 | 3/2004 | Sceusa | | 6,926,735 B2 | 8/2005 | Henderson |
| 6,709,379 B1 | 3/2004 | Brandau et al. | | 6,932,930 B2 | 8/2005 | DeSimone et al. |
| 6,709,397 B2 | 3/2004 | Taylor | | 6,936,066 B2 | 8/2005 | Palmaz et al. |
| 6,709,451 B1 | 3/2004 | Noble et al. | | 6,939,320 B2 | 9/2005 | Lennox |
| 6,710,053 B2 | 3/2004 | Naicker et al. | | 6,951,053 B2 | 10/2005 | Padilla et al. |
| 6,712,844 B2 | 3/2004 | Pacetti | | 6,953,560 B1 | 10/2005 | Castro et al. |
| 6,712,845 B2 | 3/2004 | Hossainy | | 6,953,594 B2 | 10/2005 | Lee et al. |
| 6,713,671 B1 | 3/2004 | Wang et al. | | 6,954,977 B2 | 10/2005 | Maguire et al. |
| 6,716,444 B1 | 4/2004 | Castro et al. | | 6,955,661 B1 | 10/2005 | Herweck et al. |
| 6,719,987 B2 | 4/2004 | Burrell et al. | | 6,955,685 B2 | 10/2005 | Escamilla et al. |
| 6,720,402 B2 | 4/2004 | Langer et al. | | 6,962,822 B2 | 11/2005 | Hart et al. |
| 6,723,120 B2 | 4/2004 | Yan | | 6,964,817 B2 | 11/2005 | Date et al. |
| 6,723,350 B2 | 4/2004 | Burrell et al. | | 6,971,813 B2 | 12/2005 | Shekalim et al. |
| 6,725,901 B1 | 4/2004 | Kramer et al. | | 6,972,130 B1 | 12/2005 | Lee et al. |
| 6,726,712 B1 | 4/2004 | Raeder-Devens et al. | | 6,973,718 B2 | 12/2005 | Sheppard, Jr. et al. |
| 6,730,120 B2 | 5/2004 | Berg et al. | | 6,979,346 B1 | 12/2005 | Hossainy et al. |
| 6,730,699 B2 | 5/2004 | Li et al. | | 6,979,347 B1 | 12/2005 | Wu et al. |
| 6,733,513 B2 | 5/2004 | Boyle et al. | | 6,979,348 B2 | 12/2005 | Sundar |
| 6,740,077 B1 | 5/2004 | Brandau et al. | | 6,984,404 B1 | 1/2006 | Talton et al. |
| 6,743,388 B2 | 6/2004 | Sridharan et al. | | 6,986,899 B2 | 1/2006 | Hossainy et al. |
| 6,752,826 B2 | 6/2004 | Holloway et al. | | 6,989,156 B2 | 1/2006 | Gillis |
| 6,752,829 B2 | 6/2004 | Kocur et al. | | 6,991,709 B2 | 1/2006 | Gopalraja et al. |
| 6,753,071 B1 | 6/2004 | Pacetti | | 7,001,421 B2 | 2/2006 | Cheng et al. |
| 6,758,859 B1 | 7/2004 | Dang et al. | | 7,004,968 B2 | 2/2006 | Lootz et al. |
| 6,764,505 B1 | 7/2004 | Hossainy et al. | | 7,011,670 B2 | 3/2006 | Radisch, Jr. |
| 6,764,579 B2 | 7/2004 | Veerasamy et al. | | 7,011,678 B2 | 3/2006 | Tenerz et al. |
| 6,764,709 B2 | 7/2004 | Flanagan | | 7,011,680 B2 | 3/2006 | Alt |
| 6,765,144 B1 | 7/2004 | Wang et al. | | 7,018,408 B2 | 3/2006 | Bailey et al. |
| 6,767,360 B1 | 7/2004 | Alt et al. | | 7,022,334 B1 | 4/2006 | Ding et al. |
| 6,770,086 B1 | 8/2004 | Girton | | 7,041,130 B2 | 5/2006 | Santini, Jr. |
| 6,770,729 B2 | 8/2004 | Van Antwerp | | 7,048,767 B2 | 5/2006 | Namavar |
| 6,774,278 B1 | 8/2004 | Ragheb et al. | | 7,048,939 B2 | 5/2006 | Elkins et al. |
| 6,776,022 B2 | 8/2004 | Kula et al. | | 7,052,488 B2 | 5/2006 | Uhland |
| 6,776,094 B1 | 8/2004 | Whitesides et al. | | 7,056,338 B2 | 6/2006 | Shanley et al. |
| 6,780,424 B2 | 8/2004 | Claude | | 7,056,339 B2 | 6/2006 | Elkins et al. |
| 6,783,543 B2 | 8/2004 | Jang | | 7,060,051 B2 | 6/2006 | Palasis |
| 6,790,228 B2 | 9/2004 | Hossainy et al. | | 7,060,240 B2 | 6/2006 | Costa et al. |
| 6,793,877 B1 | 9/2004 | Pettersen et al. | | 7,063,748 B2 | 6/2006 | Talton |
| 6,796,435 B2 | 9/2004 | Izumi | | 7,067,606 B2 | 6/2006 | Mather et al. |
| 6,803,070 B2 | 10/2004 | Weber | | 7,070,576 B2 | 7/2006 | O'Brien et al. |
| 6,805,709 B1 | 10/2004 | Schaldach et al. | | 7,078,108 B2 | 7/2006 | Zhang et al. |
| 6,805,898 B1 | 10/2004 | Wu et al. | | 7,099,091 B2 | 8/2006 | Taniguchi et al. |
| 6,807,440 B2 | 10/2004 | Weber | | 7,101,391 B2 | 9/2006 | Scheuermann et al. |
| RE38,653 E | 11/2004 | Igaki et al. | | 7,101,394 B2 | 9/2006 | Hamm et al. |
| 6,815,609 B1 | 11/2004 | Wang et al. | | 7,105,018 B1 | 9/2006 | Yip et al. |
| 6,820,676 B2 | 11/2004 | Palmaz et al. | | 7,105,199 B2 | 9/2006 | Blinn et al. |
| 6,827,737 B2 | 12/2004 | Hill et al. | | 7,108,716 B2 | 9/2006 | Burnside et al. |
| 6,827,966 B2 | 12/2004 | Qiu et al. | | 7,157,096 B2 | 1/2007 | Zhang et al. |
| 6,833,004 B2 | 12/2004 | Ishii et al. | | 7,160,592 B2 | 1/2007 | Rypacek et al. |

| | | |
|---|---|---|
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2 | 4/2010 | Castro et al. |
| 7,713,297 B2 | 5/2010 | Alt |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 | 1/2002 | Heublein |
| 2002/0007102 A1 | 1/2002 | Salmon et al. |
| 2002/0007209 A1 | 1/2002 | Scheerder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |

| | | | | | | |
|---|---|---|---|---|---|---|
| 2003/0158598 A1 | 8/2003 | Ashton et al. | | 2004/0191404 A1 | 9/2004 | Hossainy et al. |
| 2003/0170605 A1 | 9/2003 | Long et al. | | 2004/0202692 A1 | 10/2004 | Shanley et al. |
| 2003/0181975 A1 | 9/2003 | Ishii et al. | | 2004/0204750 A1 | 10/2004 | Dinh |
| 2003/0185895 A1 | 10/2003 | Lanphere | | 2004/0211362 A1 | 10/2004 | Castro et al. |
| 2003/0190406 A1 | 10/2003 | Hossainy et al. | | 2004/0219214 A1 | 11/2004 | Gravett et al. |
| 2003/0195613 A1 | 10/2003 | Curcio et al. | | 2004/0220510 A1 | 11/2004 | Koullick et al. |
| 2003/0204239 A1 | 10/2003 | Carlyle et al. | | 2004/0220659 A1 | 11/2004 | Girton |
| 2003/0211135 A1 | 11/2003 | Greenhalgh et al. | | 2004/0220660 A1 | 11/2004 | Shanley et al. |
| 2003/0216803 A1 | 11/2003 | Ledergerber | | 2004/0220662 A1 | 11/2004 | Dang et al. |
| 2003/0219562 A1 | 11/2003 | Rypacek et al. | | 2004/0224001 A1 | 11/2004 | Pacetti et al. |
| 2003/0221307 A1 | 12/2003 | Kaese et al. | | 2004/0225346 A1 | 11/2004 | Mazumder et al. |
| 2003/0228523 A1 | 12/2003 | DeLongchamp et al. | | 2004/0228905 A1 | 11/2004 | Greenspan et al. |
| 2003/0236513 A1 | 12/2003 | Schwarz et al. | | 2004/0230176 A1 | 11/2004 | Shanahan et al. |
| 2004/0000046 A1 | 1/2004 | Stinson | | 2004/0230225 A1 | 11/2004 | Penner et al. |
| 2004/0000540 A1 | 1/2004 | Soboyejo et al. | | 2004/0230293 A1 | 11/2004 | Yip et al. |
| 2004/0006382 A1 | 1/2004 | Sohier | | 2004/0234737 A1 | 11/2004 | Pacetti |
| 2004/0018296 A1 | 1/2004 | Castro et al. | | 2004/0236415 A1 | 11/2004 | Thomas |
| 2004/0019376 A1 | 1/2004 | Alt | | 2004/0236416 A1 | 11/2004 | Falotico |
| 2004/0022939 A1 | 2/2004 | Kim et al. | | 2004/0237282 A1 | 12/2004 | Hines |
| 2004/0024448 A1 | 2/2004 | Chang et al. | | 2004/0242106 A1 | 12/2004 | Rabasco et al. |
| 2004/0029303 A1 | 2/2004 | Hart et al. | | 2004/0243217 A1 | 12/2004 | Andersen |
| 2004/0030218 A1 | 2/2004 | Kocur et al. | | 2004/0243237 A1 | 12/2004 | Unwin et al. |
| 2004/0030377 A1 | 2/2004 | Dubson et al. | | 2004/0243241 A1 | 12/2004 | Istephanous et al. |
| 2004/0034409 A1 | 2/2004 | Heublein et al. | | 2004/0247671 A1 | 12/2004 | Prescott et al. |
| 2004/0039438 A1 | 2/2004 | Alt | | 2004/0249440 A1 | 12/2004 | Bucker et al. |
| 2004/0039441 A1 | 2/2004 | Rowland et al. | | 2004/0249443 A1 | 12/2004 | Shanley et al. |
| 2004/0044397 A1 | 3/2004 | Stinson | | 2004/0249444 A1 | 12/2004 | Reiss |
| 2004/0047980 A1 | 3/2004 | Pacetti et al. | | 2004/0249445 A1 | 12/2004 | Rosenthal et al. |
| 2004/0059407 A1 | 3/2004 | Escamilla et al. | | 2004/0249449 A1 | 12/2004 | Shanley et al. |
| 2004/0059409 A1 | 3/2004 | Stenzel | | 2004/0254419 A1 | 12/2004 | Wang et al. |
| 2004/0067301 A1 | 4/2004 | Ding | | 2004/0254635 A1 | 12/2004 | Shanley et al. |
| 2004/0071861 A1 | 4/2004 | Mandrusov et al. | | 2005/0004661 A1 | 1/2005 | Lewis et al. |
| 2004/0073155 A1* | 4/2004 | Laufer et al. ............ 604/8 | | 2005/0010275 A1 | 1/2005 | Sahatjian |
| 2004/0073284 A1 | 4/2004 | Bates et al. | | 2005/0010279 A1* | 1/2005 | Tenerz et al. ............ 623/1.16 |
| 2004/0073293 A1 | 4/2004 | Thompson | | 2005/0015142 A1 | 1/2005 | Austin et al. |
| 2004/0073297 A1 | 4/2004 | Rohde et al. | | 2005/0019265 A1 | 1/2005 | Hammer et al. |
| 2004/0073298 A1 | 4/2004 | Hossainy | | 2005/0019371 A1 | 1/2005 | Anderson et al. |
| 2004/0078071 A1 | 4/2004 | Escamilla et al. | | 2005/0021127 A1 | 1/2005 | Kawula |
| 2004/0082682 A1 | 4/2004 | Loomis et al. | | 2005/0021128 A1 | 1/2005 | Nakahama et al. |
| 2004/0088038 A1 | 5/2004 | Dehnad et al. | | 2005/0022627 A1 | 2/2005 | Chen |
| 2004/0088041 A1 | 5/2004 | Stanford | | 2005/0027350 A1 | 2/2005 | Momma et al. |
| 2004/0093071 A1 | 5/2004 | Jang | | 2005/0033407 A1 | 2/2005 | Weber et al. |
| 2004/0093075 A1 | 5/2004 | Kuehne | | 2005/0033411 A1 | 2/2005 | Wu et al. |
| 2004/0093076 A1 | 5/2004 | White et al. | | 2005/0033412 A1 | 2/2005 | Wu et al. |
| 2004/0098089 A1 | 5/2004 | Weber | | 2005/0033417 A1 | 2/2005 | Borges et al. |
| 2004/0098108 A1 | 5/2004 | Harder et al. | | 2005/0037047 A1 | 2/2005 | Song |
| 2004/0098119 A1 | 5/2004 | Wang | | 2005/0037050 A1 | 2/2005 | Weber |
| 2004/0106975 A1 | 6/2004 | Solovay et al. | | 2005/0038134 A1 | 2/2005 | Loomis et al. |
| 2004/0106984 A1 | 6/2004 | Stinson | | 2005/0038501 A1 | 2/2005 | Moore, Jr. et al. |
| 2004/0106985 A1 | 6/2004 | Jang | | 2005/0042288 A1 | 2/2005 | Koblish et al. |
| 2004/0111150 A1 | 6/2004 | Berg et al. | | 2005/0042440 A1 | 2/2005 | Bach et al. |
| 2004/0116999 A1 | 6/2004 | Ledergerber | | 2005/0055044 A1 | 3/2005 | Kangas |
| 2004/0117005 A1 | 6/2004 | Gadde et al. | | 2005/0055080 A1 | 3/2005 | Istephanous et al. |
| 2004/0117008 A1 | 6/2004 | Wnendt et al. | | 2005/0055085 A1 | 3/2005 | Rivron et al. |
| 2004/0122504 A1 | 6/2004 | Hogendijk | | 2005/0060020 A1 | 3/2005 | Jenson |
| 2004/0126566 A1 | 7/2004 | Axen et al. | | 2005/0060021 A1 | 3/2005 | O'Brien et al. |
| 2004/0133270 A1 | 7/2004 | Grandt | | 2005/0064088 A1 | 3/2005 | Fredrickson |
| 2004/0134886 A1 | 7/2004 | Wagner et al. | | 2005/0069630 A1 | 3/2005 | Fox et al. |
| 2004/0137039 A1 | 7/2004 | Sukhishvili et al. | | 2005/0070989 A1 | 3/2005 | Lye et al. |
| 2004/0138738 A1* | 7/2004 | Stinson ............ 623/1.38 | | 2005/0070990 A1 | 3/2005 | Stinson |
| 2004/0142014 A1 | 7/2004 | Litvack et al. | | 2005/0070996 A1 | 3/2005 | Dinh et al. |
| 2004/0143317 A1 | 7/2004 | Stinson et al. | | 2005/0071016 A1 | 3/2005 | Hausdorf et al. |
| 2004/0143321 A1 | 7/2004 | Litvack et al. | | 2005/0072544 A1 | 4/2005 | Palmaz et al. |
| 2004/0148010 A1 | 7/2004 | Rush | | 2005/0074479 A1 | 4/2005 | Weber et al. |
| 2004/0148015 A1 | 7/2004 | Lye et al. | | 2005/0074545 A1 | 4/2005 | Thomas |
| 2004/0153138 A1 | 8/2004 | Murphy | | 2005/0077305 A1 | 4/2005 | Guevara |
| 2004/0157073 A1 | 8/2004 | Burrell et al. | | 2005/0079132 A1 | 4/2005 | Wang et al. |
| 2004/0158308 A1 | 8/2004 | Hogendijk et al. | | 2005/0079199 A1 | 4/2005 | Heruth et al. |
| 2004/0158310 A1 | 8/2004 | Weber et al. | | 2005/0079356 A1 | 4/2005 | Rathenow et al. |
| 2004/0167572 A1 | 8/2004 | Roth et al. | | 2005/0092615 A1 | 5/2005 | Birdsall et al. |
| 2004/0167612 A1 | 8/2004 | Grignani et al. | | 2005/0096731 A1 | 5/2005 | Looi et al. |
| 2004/0172124 A1 | 9/2004 | Vallana et al. | | 2005/0100577 A1 | 5/2005 | Parker et al. |
| 2004/0181252 A1 | 9/2004 | Boyle et al. | | 2005/0100609 A1 | 5/2005 | Claude |
| 2004/0181275 A1 | 9/2004 | Noble et al. | | 2005/0102025 A1 | 5/2005 | Laroche et al. |
| 2004/0181276 A1 | 9/2004 | Brown et al. | | 2005/0106212 A1 | 5/2005 | Gertner et al. |
| 2004/0181278 A1 | 9/2004 | Tseng et al. | | 2005/0107869 A1* | 5/2005 | Sirhan et al. ............ 623/1.42 |
| 2004/0182511 A1 | 9/2004 | Rakos et al. | | 2005/0107870 A1 | 5/2005 | Wang et al. |
| 2004/0186553 A1 | 9/2004 | Yan | | 2005/0113936 A1 | 5/2005 | Brustad et al. |
| 2004/0191293 A1 | 9/2004 | Claude | | 2005/0119723 A1 | 6/2005 | Peacock |

| | | | | | | |
|---|---|---|---|---|---|---|
| 2005/0129727 A1 | 6/2005 | Weber et al. | | 2006/0035026 A1 | 2/2006 | Atanassoska et al. |
| 2005/0129731 A1 | 6/2005 | Horres et al. | | 2006/0036281 A1 | 2/2006 | Patterson et al. |
| 2005/0131509 A1 | 6/2005 | Atanassoska et al. | | 2006/0036311 A1 | 2/2006 | Nakayama et al. |
| 2005/0131521 A1 | 6/2005 | Marton | | 2006/0038027 A1 | 2/2006 | O'Connor et al. |
| 2005/0131522 A1 | 6/2005 | Stinson et al. | | 2006/0040388 A1 | 2/2006 | Bromberg et al. |
| 2005/0131527 A1 | 6/2005 | Pathak | | 2006/0041182 A1 | 2/2006 | Forbes et al. |
| 2005/0131528 A1 | 6/2005 | Buscemi et al. | | 2006/0051397 A1 | 3/2006 | Maier et al. |
| 2005/0136090 A1 | 6/2005 | Falotico et al. | | 2006/0052744 A1 | 3/2006 | Weber |
| 2005/0137677 A1 | 6/2005 | Rush | | 2006/0052863 A1 | 3/2006 | Harder et al. |
| 2005/0137679 A1 | 6/2005 | Changelian et al. | | 2006/0052864 A1 | 3/2006 | Harder et al. |
| 2005/0137684 A1 | 6/2005 | Changelian et al. | | 2006/0058868 A1 | 3/2006 | Gale et al. |
| 2005/0149169 A1 | 7/2005 | Wang et al. | | 2006/0062820 A1 | 3/2006 | Gertner et al. |
| 2005/0149170 A1 | 7/2005 | Tassel et al. | | 2006/0064160 A1 | 3/2006 | Gerold et al. |
| 2005/0149175 A1 | 7/2005 | Hunter et al. | | 2006/0067908 A1 | 3/2006 | Ding |
| 2005/0149177 A1 | 7/2005 | Weber et al. | | 2006/0069427 A1 | 3/2006 | Savage et al. |
| 2005/0159804 A1 | 7/2005 | Lad et al. | | 2006/0075044 A1 | 4/2006 | Fox et al. |
| 2005/0159805 A1 | 7/2005 | Weber et al. | | 2006/0075092 A1 | 4/2006 | Kidokoro |
| 2005/0159809 A1 | 7/2005 | Hezi-Yamit et al. | | 2006/0079958 A1 | 4/2006 | Stratford et al. |
| 2005/0160600 A1 | 7/2005 | Bien et al. | | 2006/0085062 A1 | 4/2006 | Lee et al. |
| 2005/0163821 A1 | 7/2005 | Sung et al. | | 2006/0085065 A1 | 4/2006 | Krause et al. |
| 2005/0163954 A1 | 7/2005 | Shaw | | 2006/0088566 A1 | 4/2006 | Parsonage et al. |
| 2005/0165301 A1 | 7/2005 | Smith et al. | | 2006/0088567 A1 | 4/2006 | Warner et al. |
| 2005/0165468 A1 | 7/2005 | Marton | | 2006/0088653 A1 | 4/2006 | Chappa et al. |
| 2005/0165470 A1 | 7/2005 | Weber | | 2006/0088666 A1 | 4/2006 | Kobrin et al. |
| 2005/0169969 A1 | 8/2005 | Li et al. | | 2006/0100696 A1 | 5/2006 | Atanasoska et al. |
| 2005/0171595 A1 | 8/2005 | Feldman et al. | | 2006/0115512 A1 | 6/2006 | Peacock et al. |
| 2005/0177226 A1 | 8/2005 | Banik et al. | | 2006/0118236 A1 | 6/2006 | House et al. |
| 2005/0180919 A1 | 8/2005 | Tedeschi | | 2006/0122694 A1 | 6/2006 | Stinson et al. |
| 2005/0182361 A1 | 8/2005 | Lennox | | 2006/0122697 A1 | 6/2006 | Shanley et al. |
| 2005/0182478 A1 | 8/2005 | Holman et al. | | 2006/0124472 A1 | 6/2006 | Rokicki |
| 2005/0186250 A1 | 8/2005 | Gertner et al. | | 2006/0127266 A1 | 6/2006 | Miura et al. |
| 2005/0187611 A1 | 8/2005 | Ding et al. | | 2006/0129215 A1 | 6/2006 | Helmus et al. |
| 2005/0192657 A1 | 9/2005 | Colen et al. | | 2006/0129222 A1 | 6/2006 | Stinson |
| 2005/0192662 A1 | 9/2005 | Ward | | 2006/0129225 A1 | 6/2006 | Kopia et al. |
| 2005/0192664 A1 | 9/2005 | Eisert | | 2006/0136048 A1 | 6/2006 | Pacetti et al. |
| 2005/0196424 A1 | 9/2005 | Chappa | | 2006/0141156 A1 | 6/2006 | Viel et al. |
| 2005/0208098 A1 | 9/2005 | Castro et al. | | 2006/0149352 A1 | 7/2006 | Schlum |
| 2005/0208100 A1 | 9/2005 | Weber et al. | | 2006/0153729 A1 | 7/2006 | Stinson et al. |
| 2005/0209680 A1 | 9/2005 | Gale et al. | | 2006/0155361 A1 | 7/2006 | Schomig et al. |
| 2005/0209681 A1 | 9/2005 | Curcio et al. | | 2006/0167543 A1 | 7/2006 | Bailey et al. |
| 2005/0211680 A1 | 9/2005 | Li et al. | | 2006/0177480 A1 | 8/2006 | Sung et al. |
| 2005/0214951 A1 | 9/2005 | Nahm et al. | | 2006/0178727 A1 | 8/2006 | Richter |
| 2005/0216074 A1 | 9/2005 | Sahatjian | | 2006/0184235 A1 | 8/2006 | Rivron et al. |
| 2005/0216075 A1 | 9/2005 | Wang et al. | | 2006/0193886 A1 | 8/2006 | Owens et al. |
| 2005/0220853 A1 | 10/2005 | Dao et al. | | 2006/0193887 A1 | 8/2006 | Owens et al. |
| 2005/0221072 A1 | 10/2005 | Dubrow et al. | | 2006/0193888 A1 | 8/2006 | Lye et al. |
| 2005/0222671 A1 | 10/2005 | Schaeffer et al. | | 2006/0193889 A1 | 8/2006 | Spradlin et al. |
| 2005/0228477 A1 | 10/2005 | Grainger et al. | | 2006/0193890 A1 | 8/2006 | Owens et al. |
| 2005/0228483 A1 | 10/2005 | Kaplan et al. | | 2006/0193892 A1 | 8/2006 | Furst et al. |
| 2005/0228491 A1 | 10/2005 | Snyder et al. | | 2006/0198869 A1 | 9/2006 | Furst et al. |
| 2005/0232968 A1 | 10/2005 | Palmaz et al. | | 2006/0199876 A1 | 9/2006 | Troczynski et al. |
| 2005/0233965 A1 | 10/2005 | Schwartz et al. | | 2006/0200229 A1 | 9/2006 | Burgermeister et al. |
| 2005/0234538 A1 | 10/2005 | Litvack et al. | | 2006/0200231 A1 | 9/2006 | O'Brien et al. |
| 2005/0244459 A1 | 11/2005 | DeWitt et al. | | 2006/0200233 A1 | 9/2006 | Kujawski |
| 2005/0251245 A1 | 11/2005 | Sieradzki et al. | | 2006/0210595 A1 | 9/2006 | Singhvi et al. |
| 2005/0251249 A1 | 11/2005 | Sahatjian | | 2006/0212108 A1 | 9/2006 | Tittelbach |
| 2005/0255707 A1 | 11/2005 | Hart et al. | | 2006/0222679 A1 | 10/2006 | Shanley et al. |
| 2005/0261760 A1 | 11/2005 | Weber | | 2006/0222844 A1 | 10/2006 | Stinson |
| 2005/0266039 A1 | 12/2005 | Weber | | 2006/0224237 A1 | 10/2006 | Furst et al. |
| 2005/0266040 A1 | 12/2005 | Gerberding | | 2006/0229711 A1 * | 10/2006 | Yan et al. .................... 623/1.38 |
| 2005/0266041 A1 | 12/2005 | Gerold et al. | | 2006/0229713 A1 | 10/2006 | Shanley et al. |
| 2005/0267561 A1 | 12/2005 | Jones et al. | | 2006/0230476 A1 | 10/2006 | Atanasoska et al. |
| 2005/0271703 A1 | 12/2005 | Anderson et al. | | 2006/0233941 A1 | 10/2006 | Olson |
| 2005/0271706 A1 | 12/2005 | Anderson et al. | | 2006/0241739 A1 | 10/2006 | Besselink et al. |
| 2005/0276837 A1 | 12/2005 | Anderson et al. | | 2006/0251701 A1 | 11/2006 | Lynn et al. |
| 2005/0278016 A1 | 12/2005 | Welsh et al. | | 2006/0259133 A1 | 11/2006 | Sowinski et al. |
| 2005/0278021 A1 | 12/2005 | Bates et al. | | 2006/0264138 A1 | 11/2006 | Sowinski et al. |
| 2005/0281863 A1 | 12/2005 | Anderson et al. | | 2006/0271156 A1 | 11/2006 | Ledergerber |
| 2005/0283224 A1 | 12/2005 | King | | 2006/0271168 A1 * | 11/2006 | Kleine et al. ................. 623/1.38 |
| 2005/0283229 A1 | 12/2005 | Dugan et al. | | 2006/0271169 A1 | 11/2006 | Lye et al. |
| 2005/0287188 A1 | 12/2005 | Anderson et al. | | 2006/0271192 A1 | 11/2006 | Olsen et al. |
| 2006/0002979 A1 | 1/2006 | Ashammakhi et al. | | 2006/0275554 A1 | 12/2006 | Zhao et al. |
| 2006/0009839 A1 | 1/2006 | Tan | | 2006/0276877 A1 | 12/2006 | Owens et al. |
| 2006/0013850 A1 | 1/2006 | Domb | | 2006/0276878 A1 | 12/2006 | Owens et al. |
| 2006/0014039 A1 | 1/2006 | Zhang et al. | | 2006/0276879 A1 | 12/2006 | Lye et al. |
| 2006/0015175 A1 | 1/2006 | Palmaz et al. | | 2006/0276884 A1 | 12/2006 | Lye et al. |
| 2006/0015361 A1 | 1/2006 | Sattler et al. | | 2006/0276885 A1 | 12/2006 | Lye et al. |
| 2006/0020742 A1 | 1/2006 | Au et al. | | 2006/0280770 A1 | 12/2006 | Hossainy et al. |
| 2006/0025848 A1 | 2/2006 | Weber et al. | | 2006/0287709 A1 | 12/2006 | Rao |

| | | | | | | |
|---|---|---|---|---|---|---|
| 2006/0292388 A1 | 12/2006 | Palumbo et al. | | 2008/0031765 A1 | 2/2008 | Gerold et al. |
| 2007/0003589 A1 | 1/2007 | Astafieva et al. | | 2008/0033522 A1 | 2/2008 | Grewe et al. |
| 2007/0003596 A1 | 1/2007 | Tittelbach et al. | | 2008/0033530 A1 | 2/2008 | Zberg et al. |
| 2007/0020306 A1 | 1/2007 | Schultheiss | | 2008/0033531 A1 | 2/2008 | Barthel et al. |
| 2007/0027532 A1 | 2/2007 | Wang et al. | | 2008/0033533 A1 | 2/2008 | Borck |
| 2007/0032858 A1 | 2/2007 | Santos et al. | | 2008/0033536 A1 | 2/2008 | Wittchow |
| 2007/0032862 A1 | 2/2007 | Weber et al. | | 2008/0033537 A1 | 2/2008 | Tittelbach |
| 2007/0032864 A1 | 2/2007 | Furst et al. | | 2008/0033538 A1 | 2/2008 | Borck et al. |
| 2007/0034615 A1 | 2/2007 | Kleine | | 2008/0033539 A1 | 2/2008 | Sternberg et al. |
| 2007/0036905 A1 | 2/2007 | Kramer | | 2008/0033576 A1 | 2/2008 | Gerold et al. |
| 2007/0038176 A1 | 2/2007 | Weber et al. | | 2008/0038146 A1 | 2/2008 | Wachter et al. |
| 2007/0038289 A1 | 2/2007 | Nishide et al. | | 2008/0050413 A1 | 2/2008 | Horvers et al. |
| 2007/0038290 A1 | 2/2007 | Huang et al. | | 2008/0051335 A1 | 2/2008 | Kleiner et al. |
| 2007/0045252 A1 | 3/2007 | Kleine et al. | | 2008/0051866 A1 | 2/2008 | Chen et al. |
| 2007/0048350 A1 | 3/2007 | Falotico et al. | | 2008/0051872 A1 | 2/2008 | Borck |
| 2007/0050007 A1 | 3/2007 | Kondyurin et al. | | 2008/0051881 A1 | 2/2008 | Feng et al. |
| 2007/0050009 A1 | 3/2007 | Flanagan | | 2008/0057105 A1 | 3/2008 | Atanasoska et al. |
| 2007/0052497 A1 | 3/2007 | Tada | | 2008/0058919 A1 | 3/2008 | Kramer-Brown et al. |
| 2007/0055349 A1 | 3/2007 | Santos et al. | | 2008/0058921 A1 | 3/2008 | Lindquist |
| 2007/0055354 A1 | 3/2007 | Santos et al. | | 2008/0058923 A1 | 3/2008 | Bertsch et al. |
| 2007/0055364 A1 | 3/2007 | Hossainy et al. | | 2008/0069854 A1 | 3/2008 | Xiao et al. |
| 2007/0059435 A1 | 3/2007 | Santos et al. | | 2008/0071348 A1 | 3/2008 | Boismier et al. |
| 2007/0065418 A1 | 3/2007 | Vallana et al. | | 2008/0071349 A1 | 3/2008 | Atanasoska et al. |
| 2007/0073385 A1 | 3/2007 | Schaeffer et al. | | 2008/0071350 A1 | 3/2008 | Stinson |
| 2007/0073390 A1 | 3/2007 | Lee | | 2008/0071351 A1 | 3/2008 | Flanagan et al. |
| 2007/0077163 A1 | 4/2007 | Furst et al. | | 2008/0071352 A1 | 3/2008 | Weber et al. |
| 2007/0104753 A1 | 5/2007 | Flanagan | | 2008/0071353 A1 | 3/2008 | Weber et al. |
| 2007/0106347 A1 | 5/2007 | Lin | | 2008/0071355 A1 | 3/2008 | Weber et al. |
| 2007/0106363 A1 | 5/2007 | Weber | | 2008/0071357 A1 | 3/2008 | Girton et al. |
| 2007/0123973 A1 | 5/2007 | Roth et al. | | 2008/0071358 A1 | 3/2008 | Weber et al. |
| 2007/0129789 A1 | 6/2007 | Cottone, Jr. et al. | | 2008/0082162 A1 | 4/2008 | Boismier et al. |
| 2007/0129792 A1 | 6/2007 | Picart et al. | | 2008/0086199 A1 | 4/2008 | Dave et al. |
| 2007/0134288 A1 | 6/2007 | Parsonage et al. | | 2008/0086201 A1 | 4/2008 | Weber et al. |
| 2007/0135908 A1 | 6/2007 | Zhao | | 2008/0090097 A1 | 4/2008 | Shaw et al. |
| 2007/0141106 A1 | 6/2007 | Bonutti et al. | | 2008/0097577 A1 | 4/2008 | Atanasoska et al. |
| 2007/0142897 A1 | 6/2007 | Consigny et al. | | 2008/0103589 A1 | 5/2008 | Cheng et al. |
| 2007/0142899 A1 | 6/2007 | Lootz et al. | | 2008/0103594 A1 | 5/2008 | Loffler et al. |
| 2007/0148251 A1 | 6/2007 | Hossainy et al. | | 2008/0107890 A1 | 5/2008 | Bureau et al. |
| 2007/0151093 A1 | 7/2007 | Curcio et al. | | 2008/0109072 A1 | 5/2008 | Girton |
| 2007/0156231 A1 | 7/2007 | Weber | | 2008/0113083 A1 | 5/2008 | Sutermeister et al. |
| 2007/0156248 A1 | 7/2007 | Marco et al. | | 2008/0124373 A1 | 5/2008 | Xiao et al. |
| 2007/0160641 A1 | 7/2007 | Jang | | 2008/0131479 A1 | 6/2008 | Weber et al. |
| 2007/0168016 A1 | 7/2007 | Gronemeyer et al. | | 2008/0140172 A1 | 6/2008 | Carpenter et al. |
| 2007/0173923 A1 | 7/2007 | Savage et al. | | 2008/0140186 A1 | 6/2008 | Grignani et al. |
| 2007/0178129 A1 | 8/2007 | Flanagan | | 2008/0145400 A1 | 6/2008 | Weber et al. |
| 2007/0181433 A1 | 8/2007 | Birdsall et al. | | 2008/0147175 A1 | 6/2008 | Krivoruchko et al. |
| 2007/0184083 A1 | 8/2007 | Coughlin | | 2008/0147177 A1 | 6/2008 | Scheuermann et al. |
| 2007/0190104 A1 | 8/2007 | Kamath et al. | | 2008/0152929 A1 | 6/2008 | Zhao |
| 2007/0191923 A1 | 8/2007 | Weber | | 2008/0160166 A1 | 7/2008 | Rypacek et al. |
| 2007/0191928 A1 | 8/2007 | Rolando et al. | | 2008/0160259 A1 | 7/2008 | Nielson et al. |
| 2007/0191931 A1 | 8/2007 | Weber | | 2008/0161906 A1 | 7/2008 | Atanasoska et al. |
| 2007/0191943 A1 | 8/2007 | Shrivastava et al. | | 2008/0171929 A1 | 7/2008 | Katims |
| 2007/0197980 A1 | 8/2007 | Barry et al. | | 2008/0175885 A1 | 7/2008 | Asgari |
| 2007/0202466 A1 | 8/2007 | Schwarz et al. | | 2008/0177378 A1 | 7/2008 | Asgari |
| 2007/0207186 A1 | 9/2007 | Scanlon et al. | | 2008/0183269 A2 | 7/2008 | Kaplan et al. |
| 2007/0208412 A1 | 9/2007 | Elmaleh | | 2008/0183277 A1* | 7/2008 | Atanasoska et al. ......... 623/1.15 |
| 2007/0219626 A1 | 9/2007 | Rolando et al. | | 2008/0183278 A1 | 7/2008 | Atanasoska et al. |
| 2007/0224116 A1 | 9/2007 | Chandrasekaran et al. | | 2008/0188927 A1 | 8/2008 | Rohde et al. |
| 2007/0224244 A1 | 9/2007 | Weber et al. | | 2008/0195170 A1 | 8/2008 | Asgari |
| 2007/0225799 A1 | 9/2007 | Doty | | 2008/0195189 A1 | 8/2008 | Asgari |
| 2007/0244541 A1 | 10/2007 | Schulman | | 2008/0195198 A1 | 8/2008 | Asgari |
| 2007/0244569 A1 | 10/2007 | Weber et al. | | 2008/0208308 A1 | 8/2008 | Allen et al. |
| 2007/0250155 A1 | 10/2007 | Simpson | | 2008/0208313 A1 | 8/2008 | Yu et al. |
| 2007/0250156 A1 | 10/2007 | Palmaz | | 2008/0208352 A1 | 8/2008 | Krivoruchko et al. |
| 2007/0250158 A1 | 10/2007 | Krivoruchko et al. | | 2008/0213377 A1 | 9/2008 | Bhatia et al. |
| 2007/0255388 A1 | 11/2007 | Rudakov et al. | | 2008/0215129 A1 | 9/2008 | Venturelli et al. |
| 2007/0255392 A1 | 11/2007 | Johnson | | 2008/0215139 A1 | 9/2008 | McMorrow et al. |
| 2007/0264199 A1 | 11/2007 | Labhasetwar et al. | | 2008/0215140 A1 | 9/2008 | Borck et al. |
| 2007/0264303 A1 | 11/2007 | Atanasoska et al. | | 2008/0241218 A1 | 10/2008 | McMorrow et al. |
| 2007/0270940 A1 | 11/2007 | Doty | | 2008/0243113 A1 | 10/2008 | Shastri et al. |
| 2007/0270942 A1 | 11/2007 | Thomas | | 2008/0243230 A1 | 10/2008 | Lootz et al. |
| 2007/0281073 A1 | 12/2007 | Gale et al. | | 2008/0243231 A1 | 10/2008 | Flanagan et al. |
| 2007/0281117 A1 | 12/2007 | Kaplan et al. | | 2008/0243234 A1 | 10/2008 | Wilcox |
| 2007/0282432 A1 | 12/2007 | Stinson et al. | | 2008/0243240 A1 | 10/2008 | Doty et al. |
| 2007/0299509 A1 | 12/2007 | Ding | | 2008/0243242 A1 | 10/2008 | Kappelt et al. |
| 2007/0299512 A1 | 12/2007 | Korzuschnik et al. | | 2008/0249600 A1 | 10/2008 | Atanasoska et al. |
| 2008/0003251 A1 | 1/2008 | Zhou | | 2008/0249615 A1 | 10/2008 | Weber |
| 2008/0003256 A1 | 1/2008 | Martens et al. | | 2008/0255508 A1 | 10/2008 | Wang |
| 2008/0004691 A1 | 1/2008 | Weber et al. | | 2008/0255509 A1 | 10/2008 | Wang |

| | | | | | | |
|---|---|---|---|---|---|---|
| 2008/0262589 A1 | 10/2008 | Nagura | | 2009/0281613 A1 | 11/2009 | Atanasoska et al. |
| 2008/0269872 A1 | 10/2008 | Lootz et al. | | 2009/0287301 A1 | 11/2009 | Weber |
| 2008/0288048 A1 | 11/2008 | Rolando et al. | | 2009/0287302 A1 | 11/2009 | Thomas et al. |
| 2008/0290467 A1 | 11/2008 | Shue | | 2009/0306584 A1 | 12/2009 | Schmidtlein et al. |
| 2008/0294236 A1 | 11/2008 | Anand et al. | | 2009/0306756 A1 | 12/2009 | Cho et al. |
| 2008/0294246 A1 | 11/2008 | Scheuermann | | 2009/0306765 A1 | 12/2009 | Weber |
| 2008/0306584 A1 | 12/2008 | Kramer-Brown | | 2009/0306766 A1 | 12/2009 | McDermott et al. |
| 2009/0005862 A1 | 1/2009 | Nakatani et al. | | 2009/0311300 A1 | 12/2009 | Wittchow |
| 2009/0012599 A1 | 1/2009 | Broome et al. | | 2009/0312807 A1 | 12/2009 | Boudreault et al. |
| 2009/0018639 A1 | 1/2009 | Kuehling | | 2009/0319035 A1 | 12/2009 | Terry |
| 2009/0018647 A1 | 1/2009 | Benco et al. | | 2009/0324684 A1 | 12/2009 | Atanasoska et al. |
| 2009/0018648 A1 | 1/2009 | Wittchow | | 2009/0326638 A1 | 12/2009 | Atanasoska et al. |
| 2009/0024199 A1 | 1/2009 | Birdsall et al. | | 2010/0008970 A1* | 1/2010 | O'Brien et al. ................ 424/426 |
| 2009/0024209 A1 | 1/2009 | Ozdil et al. | | 2010/0010621 A1 | 1/2010 | Klocke |
| 2009/0024210 A1 | 1/2009 | Klocke et al. | | 2010/0010640 A1 | 1/2010 | Gerold et al. |
| 2009/0024211 A1 | 1/2009 | Wittchow | | 2010/0015206 A1 | 1/2010 | Flanagan et al. |
| 2009/0028785 A1 | 1/2009 | Clarke | | 2010/0016940 A1 | 1/2010 | Shokoohi et al. |
| 2009/0030494 A1 | 1/2009 | Stefanadis et al. | | 2010/0021523 A1 | 1/2010 | Scheuermann et al. |
| 2009/0030500 A1 | 1/2009 | Weber et al. | | 2010/0023112 A1 | 1/2010 | Borck et al. |
| 2009/0030504 A1 | 1/2009 | Weber et al. | | 2010/0023116 A1 | 1/2010 | Borck et al. |
| 2009/0030506 A1 | 1/2009 | Klocke et al. | | 2010/0028436 A1 | 2/2010 | Ohrlander et al. |
| 2009/0030507 A1 | 1/2009 | Klocke et al. | | 2010/0030326 A1 | 2/2010 | Radhakrishnan et al. |
| 2009/0035351 A1 | 2/2009 | Berglund et al. | | 2010/0034899 A1 | 2/2010 | Harder et al. |
| 2009/0043330 A1 | 2/2009 | To | | 2010/0042205 A1 | 2/2010 | Atanasoska et al. |
| 2009/0043374 A1 | 2/2009 | Nakano | | 2010/0042206 A1 | 2/2010 | Yadav et al. |
| 2009/0043380 A1 | 2/2009 | Blaha et al. | | 2010/0047312 A1 | 2/2010 | Wittchow |
| 2009/0048660 A1 | 2/2009 | Adden | | 2010/0047324 A1 | 2/2010 | Fritz et al. |
| 2009/0062905 A1 | 3/2009 | Moore, Jr. et al. | | 2010/0049146 A1 | 2/2010 | Nielsen et al. |
| 2009/0069884 A1 | 3/2009 | Mueller | | 2010/0049296 A1 | 2/2010 | Sarasam et al. |
| 2009/0076588 A1 | 3/2009 | Weber | | 2010/0049299 A1 | 2/2010 | Popowski et al. |
| 2009/0076596 A1 | 3/2009 | Adden et al. | | 2010/0049300 A1 | 2/2010 | Harder |
| 2009/0081293 A1 | 3/2009 | Murase et al. | | 2010/0055151 A1 | 3/2010 | Flanagan |
| 2009/0081450 A1 | 3/2009 | Ascher et al. | | 2010/0057188 A1 | 3/2010 | Weber |
| 2009/0088831 A1 | 4/2009 | Goto | | 2010/0057197 A1 | 3/2010 | Weber et al. |
| 2009/0088834 A1 | 4/2009 | Wang | | 2010/0070024 A1 | 3/2010 | Venturelli et al. |
| 2009/0093871 A1 | 4/2009 | Rea et al. | | 2010/0075162 A1 | 3/2010 | Yang et al. |
| 2009/0095715 A1 | 4/2009 | Sabaria | | 2010/0076544 A1 | 3/2010 | Hoffmann et al. |
| 2009/0118809 A1 | 5/2009 | Scheuermann et al. | | 2010/0076556 A1 | 3/2010 | Tomantschger et al. |
| 2009/0118812 A1 | 5/2009 | Kokate et al. | | 2010/0081735 A1 | 4/2010 | Mao et al. |
| 2009/0118813 A1 | 5/2009 | Scheuermann et al. | | 2010/0082092 A1 | 4/2010 | Gerold |
| 2009/0118814 A1 | 5/2009 | Schoenle et al. | | 2010/0087910 A1 | 4/2010 | Weber |
| 2009/0118815 A1 | 5/2009 | Arcand et al. | | 2010/0087911 A1 | 4/2010 | Mueller |
| 2009/0118818 A1 | 5/2009 | Foss et al. | | 2010/0087914 A1 | 4/2010 | Bayer et al. |
| 2009/0118819 A1 | 5/2009 | Merz et al. | | 2010/0087915 A1 | 4/2010 | Bayer et al. |
| 2009/0118820 A1 | 5/2009 | Gregorich et al. | | 2010/0087916 A1 | 4/2010 | Bayer et al. |
| 2009/0118821 A1 | 5/2009 | Scheuermann et al. | | 2010/0092535 A1 | 4/2010 | Cook et al. |
| 2009/0118822 A1 | 5/2009 | Holman et al. | | 2010/0106243 A1 | 4/2010 | Wittchow |
| 2009/0118823 A1 | 5/2009 | Atanasoska et al. | | 2010/0119576 A1 | 5/2010 | Harder et al. |
| 2009/0123517 A1 | 5/2009 | Flanagan et al. | | 2010/0119581 A1 | 5/2010 | Gratz et al. |
| 2009/0123521 A1 | 5/2009 | Weber et al. | | 2010/0121432 A1 | 5/2010 | Klocke et al. |
| 2009/0124956 A1 | 5/2009 | Swetlin et al. | | 2010/0125325 A1 | 5/2010 | Allen et al. |
| 2009/0131540 A1 | 5/2009 | Hiromoto et al. | | 2010/0125328 A1 | 5/2010 | Flanagan |
| 2009/0143855 A1 | 6/2009 | Weber et al. | | 2010/0131050 A1 | 5/2010 | Zhao |
| 2009/0149942 A1 | 6/2009 | Edelman et al. | | 2010/0131052 A1 | 5/2010 | Kappelt et al. |
| 2009/0157165 A1 | 6/2009 | Miller et al. | | 2010/0161031 A1 | 6/2010 | Papirov et al. |
| 2009/0157172 A1 | 6/2009 | Kokate et al. | | 2010/0217370 A1 | 8/2010 | Scheuermann et al. |
| 2009/0164002 A1 | 6/2009 | Becher et al. | | | | |
| 2009/0171452 A1 | 7/2009 | Yamamoto et al. | | FOREIGN PATENT DOCUMENTS | | |
| 2009/0177273 A1 | 7/2009 | Piveteau et al. | | | | |
| 2009/0182290 A1 | 7/2009 | Harder et al. | | AU | 2003 203 722 | 11/2003 |
| 2009/0182337 A1 | 7/2009 | Stopek et al. | | CA | 2 235 031 | 10/1998 |
| 2009/0182425 A1 | 7/2009 | Duda et al. | | CA | 2 346 857 | 5/2000 |
| 2009/0192571 A1 | 7/2009 | Stett et al. | | CA | 2 371 800 | 8/2000 |
| 2009/0192594 A1 | 7/2009 | Borck | | DE | 198 11 033 | 8/1999 |
| 2009/0192595 A1 | 7/2009 | Nagura et al. | | DE | 198 56 983 | 12/1999 |
| 2009/0192596 A1 | 7/2009 | Adden | | DE | 103 57 281 | 7/2005 |
| 2009/0196899 A1 | 8/2009 | Birdsall et al. | | DE | 103 61 941 | 7/2005 |
| 2009/0198320 A1 | 8/2009 | Mueller et al. | | DE | 10 2006 038236 | 2/2008 |
| 2009/0202610 A1 | 8/2009 | Wilson | | DE | 10 2006 38236 | 2/2008 |
| 2009/0204203 A1 | 8/2009 | Allen et al. | | EP | 0 006 544 | 6/1979 |
| 2009/0208428 A1 | 8/2009 | Hill et al. | | EP | 0 337 035 | 10/1989 |
| 2009/0208555 A1* | 8/2009 | Kuttler et al. ................ 424/426 | | EP | 0 923 389 | 7/1998 |
| 2009/0214373 A1 | 8/2009 | Stinson et al. | | EP | 0 923 912 | 6/1999 |
| 2009/0228037 A1 | 9/2009 | Rego | | EP | 0 966 979 | 12/1999 |
| 2009/0240323 A1 | 9/2009 | Wilcox | | EP | 0 972 563 | 1/2000 |
| 2009/0254171 A1 | 10/2009 | Heikkila | | EP | 1 054 644 | 11/2000 |
| 2009/0259300 A1 | 10/2009 | Dorogy, Jr. et al. | | EP | 1 071 490 | 1/2001 |
| 2009/0270979 A1 | 10/2009 | Adden | | EP | 1 222 901 | 7/2002 |
| 2009/0274737 A1 | 11/2009 | Borck | | EP | 1 260 214 | 11/2002 |
| | | | | EP | 1 270 023 | 1/2003 |

| | | |
|---|---|---|
| EP | 1 273 314 | 1/2003 |
| EP | 1 370 306 | 12/2003 |
| EP | 1 389 471 | 2/2004 |
| EP | 1 393 766 | 3/2004 |
| EP | 1 419 793 | 5/2004 |
| EP | 0 951 877 | 6/2004 |
| EP | 0 875 218 | 2/2005 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | WO 93/04118 | 3/1993 |
| WO | WO 97/11724 | 4/1997 |
| WO | 98/29025 | 7/1998 |
| WO | WO 98/48851 | 11/1998 |
| WO | 99/33410 | 7/1999 |
| WO | WO 99/47077 | 9/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | 00/54704 | 9/2000 |
| WO | WO 00/66190 | 11/2000 |
| WO | WO 01/49338 | 7/2001 |
| WO | WO 01/78906 | 10/2001 |
| WO | 01/80920 | 11/2001 |
| WO | 01/87371 | 11/2001 |
| WO | WO 02/45764 | 6/2002 |
| WO | WO 02/47739 | 6/2002 |
| WO | WO 02/053202 | 7/2002 |
| WO | 03/002243 | 1/2003 |
| WO | WO 03/013396 | 2/2003 |
| WO | 03/035134 | 5/2003 |
| WO | WO 03/035131 | 5/2003 |
| WO | WO 03/035278 | 5/2003 |
| WO | WO 03/063733 | 8/2003 |
| WO | WO 03/094990 | 11/2003 |
| WO | 2004/029313 | 4/2004 |
| WO | 2004/043292 | 5/2004 |
| WO | WO 2004/093643 | 11/2004 |
| WO | 2005/025449 | 3/2005 |
| WO | WO 2005/065576 | 7/2005 |
| WO | WO 2005/065576 A1 * | 7/2005 |
| WO | 2005/079335 | 9/2005 |
| WO | WO 2005/110395 | 11/2005 |
| WO | WO 2005/118019 | 12/2005 |
| WO | WO 2006/008739 | 1/2006 |
| WO | WO 2006/060033 | 6/2006 |
| WO | WO 2006/060534 | 6/2006 |
| WO | WO 2006/065356 | 6/2006 |
| WO | 2006/077154 | 7/2006 |
| WO | 2006/080381 | 8/2006 |
| WO | 2006/097503 | 9/2006 |
| WO | 2006/104644 | 10/2006 |
| WO | WO 2006/108065 | 10/2006 |
| WO | WO 2007/005806 | 1/2007 |
| WO | 2007/013102 | 2/2007 |
| WO | WO 2007/018931 | 2/2007 |
| WO | 2007/035791 | 3/2007 |
| WO | WO 2007/024552 | 3/2007 |
| WO | 2007/079363 | 7/2007 |
| WO | 2007/079636 | 7/2007 |
| WO | WO 2007/082147 | 9/2007 |
| WO | 2007/139668 | 12/2007 |
| WO | 2008/003450 | 3/2008 |
| WO | 2008/036457 | 3/2008 |
| WO | 2008/036548 | 3/2008 |
| WO | 2008/036554 | 3/2008 |
| WO | WO 2008/062414 | 5/2008 |
| WO | 2008/092436 | 8/2008 |
| WO | 2008/106271 | 9/2008 |
| WO | 2008/118606 | 10/2008 |
| WO | WO 2008/117315 | 10/2008 |

OTHER PUBLICATIONS

Ferrando, "Review of Corrosion and Corrosion Control of Magnesium Alloys and Composites," *J. Mater. Eng.*, 1989, 11:299-313.

Gray and Luan, "Protective coatings on magnesium and its alloys—a critical review," *J. Alloys. Compounds*, 2002, 336:88-113.

International Search Report/Written Opinion in PCT/US2007078411 mailed Mar. 6, 2008, 12 pages.

Park et al., "Microstructural change and precipitation hardening in melt-spun Mg-X-Ca alloys," *Science and Technology of Advanced Materials*, 2001, 2:73-78.

Straumal et al., "Vacuum arc deposition of protective layers on glass and polymer substrates," *Thin. Solid Films*, 2001, 383:224-226.

Wang et al., "Nonlinear optical properties of thin iron films grown on MgO (100) by pulsed laser deposition," *Thin Solid Films*, 2005, 471:86-90.

European Examiner Melanie Geuer, International Preliminary Report on Patentability received in PCT/US2007/078411, mailed Apr. 2, 2009, 8 pages.

U.S. Appl. No. 10/849,742, filed May 20, 2004, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.

"Galvanic cell" printout from wikipedia, 2 pgs, printed Oct. 28, 2005.

"Galvanic corrosion", http://www.corrosion-doctors.org/Aircraft/galvdefi.htm, 3 pgs., printed Oct. 28, 2005.

"Galvanic series" printout from Wikipedia, p. 1 of 2, printed Oct. 28, 2005.

"Best of the ACC Scientific Session 2002," Rev. Cardiovasc. Med., 2002, 3(2):85-104.

"Corrosion Theory and Corrosion Protection," *EM*1110-3400, 1995, 8 pages.

Aghion et al., "Newly Developed Magnesium Alloys for Powertrain Applications," *JOM*, 2003, p. 30.

Andión et al., "Corrosion behaviour at the interface of steel bars embedded in cement slurries. Effect of phenol polymer coatings," *Corrosion Science*, 2002, 44:2805-2816.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability," *Advances in Colloid and Interface Science*, 2004, 111:49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Baurschmidt et al., "The Electrochemical Aspects of the Thrombogenicity of a Material," *J. Bioengineering*, 1977, 1:261-278.

Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.

Berry et al., "Functionalisation of magnetic nanoparticles for applications in biomedicine," *J. Phys. D: Appl. Phys.*, 2003, 36:R198-R206.

Bolz et al., "Effect of smooth, porous and fractal surface structure on the properties of an interface," *J. Materials Science: Materials in Medicine*, 1995, 6:844-848.

Brandau et al., "Nanoporous Ceramic Coatings for Synthesis of Radioactive Implants," *Journal of Nuclear Medicine Abstract Book*, June 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HCl by eugenol derivatives," *Applied Surface Science*, 2005, 246:199-206.

Changwen et al., "Polyoxometalate-based organic-inorganic hybrid materials"; http://www.solgel.com/articles/oct01/changwen.asp, Retrieved from the Internet on Nov. 1, 2004 (17 pages).

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Examiner John De Bruijn, International Search Report/Written Opinion in PCT/US05/16600 mailed May 4, 2006, 15 pages.

Examiner Beate Giffo-Schmitt, International Preliminary Report on Patentability in PCT/US05/16600 mailed Nov. 30, 2006, 7 pages.

Examiner M. Sierra Gonzalez, International Preliminary Report on Patentability in PCT/US07/78476 mailed Mar. 26, 2009, 7 pages.

Authorized Officer Simin Baharlou, International Search Report/Written Opinion in PCT/US07/66568 mailed Oct. 8, 2007, 11 pages.

Authorized Officer Simin Baharlou, International Preliminary Report on Patentability in PCT/US07/66568 mailed Oct. 23, 2008, 10 pages.

Examiner Melanie Geuer, International Search Report/Written Opinion in PCT/US07/78505 mailed Mar. 4, 2008, 10 pages.

Examiner Melanie Geuer, International Preliminary Report on Patentability in PCT/US07/78505 mailed Mar. 26, 2009, 7 pages.

Authorized Officer Athina Nickitas-Etienne, International Search Report/Written Opinion in PCT/US07/78449, mailed Jan. 13, 2009, 24 pages.

Authorized Officer Athina Nickitas-Etienne, International Preliminary Report on Patentability in PCT/US07/78449 mailed Mar. 26, 2009, 9 pages.

Authorized Officer Simin Baharlou, International Preliminary Report on Patentability in PCT/US07/75072 mailed Feb. 12, 2009, 9 pages.

Examiner Véronique van Loon-Mégard, International Search Report/Written Opinion in PCT/US07/78429 mailed Mar. 28, 2008, 13 pages.

Examiner Véronique van Loon-Mégard International Preliminary Report on Patentability in PCT/US07/78429 mailed Apr. 2, 2009, 8 pages.

Authorized Officer Elisabeth Reinecke, International Search Report/Written Opinion in PCT/US07/60137 mailed Jul. 27, 2007, 20 pages.

Examiner Melanie Geuer, International Preliminary Report on Patentability in PCT/US07/78412 mailed Apr. 2, 2009, 7 pages.

Authorized Officer Trudy Hinterwimmer, International Search Report/Written Opinion in PCT/US07/78412 mailed Mar. 3, 2008, 10 pages.

Authorized Officer Joëlle Gerber, International Search Report/Written Opinion in PCT/US07/78450 mailed Nov. 19, 2008, 17 pages.

Examiner Sierra Gonzalez, International Preliminary Report on Patentability in PCT/US07/78450 mailed Mar. 26, 2009, 7 pages.

Examiner Josephina Tschuck, International Search Report/Written Opinion in PCT/US07/73839 mailed Apr. 16, 2008, 17 pages.

Examiner Josephina Tschuck, International Preliminary Report on Patentability in PCT/US07/73839 mailed 2 Apr. 2, 2009, 10 pages.

Authorized Officer Cecilia Giel-Barragán Ramos, International Search Report/Written Opinion in PCT/US07/79841 mailed Feb. 4, 2009, 21 pages.

Authorized Officer Athina Nickitas-Etienne, International Preliminary Report on Patentability in PCT/US07/79841 mailed Apr. 30, 2009, 7 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

Authorized Officer Véronique van Loon-Mégard, International Search Report/Written Opinion in PCT/US08/75976 mailed Nov. 25, 2008, 20 pages.

Authorized Officer Trudy Hinterwimmer, International Search Report/Written Opinion in PCT/US09/49422 mailed Aug. 24, 2009, 10 pages.

Damiani et al., "Vasorelaxant effects on eugenol on rat thoracic aorta," *Vascular Pharmacol.*, 2003, 40:59-66.

Dexter, "Galvanic Corrosion," MAS Note, University of Delaware Sea Grant Marine Advisory Service, 2003.

Di Mario et al., "Moonlight: a controlled registry of an iridium-oxide coated stent with angiographic follow up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duygu, "Controlled Release Systems," http://www.biomed.metu.edu.tr/courses/term_papers/contr-rel-sys_duygu.htm Dec. 30, 2005.

Eniola and Hammer, "Characterization of biodegradable drug delivery vehicles with the adhesive properties of leukocytes II: effect of degradation on targeting activity," *Biomaterials*, 2005, 26:661-670.

Farhat et al., "Corrosion Control Using Polyelectrolyte Multilayers," *Electrochemical and Solid State Letters*, 2002, 5(4):B13-B15.

Ferrando, "Review of Corrosion and Corrosion Control of Magnesium Alloys and Composites," *J. Mater. Eng.*, 1989, 11:299-313.

Fischer et al., "Hydrogen in magnesium alloys and magnesium interfaces: preparation, electronic properties and interdiffusion," *J. Less Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Frei, "On the Role of Vitamin C and Other Antioxidants in Atherogenesis and Vascular Dysfunction," *Proceedings—Society for Experimental Biology and Medicine*, 1999, 222:196-204.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Guo et al., "Multi-layer LB films of single-wall carbon nanotubes," *Physica B*, 2002, 323:235-236.

Guo et al., "Manipulation of single-wall carbon nanotubes into aligned molecular layers," *Chem. Phys. Lett.*, 2002, 362:314-318.

Gurib-Fakim, "Medicinal plants: Traditions of yesterday and drugs of tomorrow," *Molecular Aspects of Medicine*, 2006, 27:1-93.

Haferkamp et al., "Magnesium-Base-Alloys as Implant-Material Steps to the Production of Thin Components," *Magnesium*, 2000, 159-164.

Hau et al., "Surface-Chemistry Technology for Microfluidics," *J. Micromech. Microeng.*, 2003, 13:272-278.

Huang et al., "A Review on Polymer Nanofibers by Electro-spinning and their Applications in Nanocomposites," *Composites Science & Technology*, 2003, 63:2223-2253.

Heublein et al., "Biocorrosion of magnesium alloys: a new principle in cardiovascular implant technology?" *Heart*, 2003, 89:651-656.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Local Tissue Engineering by Biocorrosion Vision or Reality?" *The American Journal of Cardiology, TCT Abstracts/Poster*, Oct. 16, 2000.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jiang, "A review of wet impregnation—An alternative method for the fabrication of high performance and nano-structured electrodes of solid oxide fuel cells," *Materials Science and Engineering A*, 2006, 418:199-210.

Kean and Davies, "Cathodic Protection," 7 pages, 1981; http://www.np1.co.uk/upload/pdf/cathodic_protection.pdf.

Kim et al., "Comprehensive study on vitamin C equivalent antioxidant capacity (VCEAC) of various polyphenols in scavenging a free radical and its structural relationship," *Crit. Rev, Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.

Lambert et al., "Inhibition of carcinogenesis by polyphenols: evidence from laboratory investigations," *Am. J. Clin. Nutr.*, 2005, 81:284S-291S.

Lee et al., "Retentive and compressive strengths of modified zinc oxide-eugenol cements," *J. Dentistry*, 2000, 28:69-75.

Liao et al., "Fabrication of porous biodegradable polymer scaffolds using a solvent merging/particulate leaching method," *J. Biomed. Mater. Res.*, 2002, 59(4):676-681.

Lin et al., "Micropatterning proteins and cells on polylactic acid and poly(lactide-*co*-glycolide)," *Biomaterials*, 2005, 26:3655-3662.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, $7^{th}$ European Conference on Advanced Materials and Processes*, Jun. 10-14, 2001 (Abstract).

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86(5):.

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis* 1965, pp. 337-348.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook vol. 13A: Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilites," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Suhaj, "Spice antioxidants isolation and their antiradical activityL a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Characterisation of Severely Deformed Austenitic Stainless Steel Wire," *Matericals Science and Technology*, 2005, 21:1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaC l aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Zeta Potential-An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Natural Polyelectrolyte Films Based on Layer-by-Layer Deposition of Collagen and Hyaluronic Acid," *Biomaterials*, 2005, 26:3353-3361.

Zhang et al., "Improving multilayer films endurance by photoinduced interaction between Dawson-type polyoxometalate and diazo resin," *Materials Chemistry and Physics*, 2005, 90:57-52.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zhou et al., "Drug-loaded, Magnetic, hollow silica nanocomposites for nanomedicine," *Nanomedicine: Nanotechnology, Biology and Medicine*, 2005, 1:233-237.

Zucchi et al., "Influence of a silane treatment on the corrosion resistance of a WE43 magnesium allow," *Surface Coatings Technol.*, 2006, 200:4136-4143.

U.S. Appl. No. 6,533,715, filed Mar. 2003, Hossainy et al.

Aaltonen, "Atomic Layer Deposition of Noble Metal Thin Films," *University of Helsinki*, Apr. 8, 2005, pp. 1-71.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," 2003 *Aerospace Coatings Removel and Coatings Conference*, May 20-22, 2003, Colorado Springs, CO, 7 pages.

Ashtari et al. "An efficient method for recovery of target ssDNA based on amino-modified silica-coated magnetic nanoparticles" *Talanta* 67. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Authorized officer Athina Nickitas-Etienne, International Preliminary Report on Patentability in PCT/US08/86639 mailed Jun. 24, 2010, 2 pages.

International Search Report/Written Opinion in PCT/US2008/86639 mailed Feb. 23, 2010, 8 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless stell," *Progress in Organic Coatings*, 2005, 54: 63-72.

Bernkop-Schnurch, "Chitosan and its derivatives: potential excipients for peroral peptide delivery systems," *International J. Of Pharmaceutics*, 2000, 194: 1-13.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bosiers et al., "Absorbable Metal stent for CLI in Infrapopliteal lesions: 1 year results," *CX 2005 Global Endovascular Forum*, Apr. 2005, pp. 1-23.

Brunatto and Muzart, "Influence of the gas mixture flow on the processing parameters of hollow cathode discharge ion sintering," *J. Phys. D.: Appl. Phys*., 2007, 40: 3937-3944.

Brunner et al., "Porosity Tailored Growth of Black Anodic Layers on Magnesium in an Organic Electrolyte," Journal of the Electrochemical Society, vol. 156 (2), Dec. 12, 2008, pp. C62-C66.

Chang et al., "Effect of Heat Treatment on Corrosion and Electrochemical behavior of Mg-3Nd-0.2Zn-0.4Zr (wt. %) alloy," *Science Direct, Electrochimica Acta* 52, 2007, 3160-3167.

Chang et al., "Templated sythesis of Gold-iron Alloy nanoparticles using pulsed laser deposition," *Nanotechnology*, vol. 17, 2006, pp. 5131-5135.

Chen et al., "Laser Cladding of Mg20A18o Powder on ZM5 Magnesium Alloys," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}^{3-}$ (x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Cogger et al. "An Introduction to Electrochemical Impedance Measurement," *Solarton Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Davies, "Changing the salt, changing the drug," *The Pharmaceutical Journal*, 2001, 266: 322-323.

De Geest et al., "Self-rupturing Microcapsules," *Adv. Mater*., 2005, vol. 17, pp. 2357-2361.

de Witte, "Analysis of the principal component of external casing corrosion in deep wells," *J. Appl. Electrochem*., 1985, 15: 325-334.

Di Mario et al., "Drug-eluting bioabsorbable magnesium stent," *J. Interventional Cardiol*., 2004, 17(6): 391-395.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Eggebrecht et al., "Novel Magnetic Resonance-Compatible Coronary Stent: The Absorbable Magnesium-Alloy Stent," *Circulation*, 2005, 112: 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-75.

Erne et al., "The Road to Bioabsorbable Stents: Reaching Clinical Reality?" *Cardio Vascular and Interventional Radiology*, Sep. 26, 2005, pp. 11-16.

European Examiner Marie-France Weiss, International Preliminary report on Patentability received in PCT/US2007/078417, mailed Mar. 26, 2009, 8 pages.

European Examiner Melanie Geuer, International Preliminary Report on Patentability, received in PCT/US2007/078407, mailed Mar. 26, 2009, 6 pages.

European Search Report from EP 10159664.1, mailed Jun. 4, 2010, 3 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Madern Physics B*, vol. 17, No. 8 & 9, 2003, pp. 1601-1607.

Fischer et al., "Determination of in-vivo corrosion rates of degradable implants by SR-microtomography," date unknown, pp. 1-2.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.

Fraunhofer IIS—Poster (German), "Prinzip der hochauflosenden Comptuertomographie," 2009, 1 page.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of *in vivo* corrosion rates in baboons, and correlation with *in vitro* tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Griffiths et al., "Future devices: bioabsorbable stents," *Br. J. (Acute & Interventional Cardiology)*, 2004, 11: AIC80-AIC84.

Grube, "Bioabsorbable Stents-The Boston Scientific & REVA Technology," *EuroPCR2009*, pp. 1-27.

Gu et al., "In vitro Corrosion and biocompatibility of binary magnesium alloys," *Biomaterials*, vol. 30, 2009, pp. 484-498.

Gupta et al., "Nanometer spaced electrodes using selective area atomic layer deposition," *Applied Physics Letters*, vol. 90, 2007, pp. 1-4.

Haenzi et al., "Design strategy for microalloyed ultra-ductile Mg alloys," 2009, *Phil. Mag. Letters*, 89(6): 377-390.

Haenzi et al., "Design strategy for new biodegradable Mg-Y-Zn alloys for medical applications," *Int. J. Mat. Res.*, 2009, 100: 1127-1136.

Haenzi et al., "On the biodegradation performance of an Mg-Y-RE alloy with various surface conditions in simulated body fluid," *Acto Biomat.*, 2009, 5: 162-171.

Hamu et al., "Influence of Si, Ca and Ag addition on corrosion behavior of new wrought Mg-Zn alloys," 2006, 22(10): 1213-1218.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg-Y-Zn alloys for medical applications," *Int. J. Mat. Res.*, vol. 100, 2009, pp. 1127-1136.

Hänzi et al., "On the biodegradation performance of an Mg-Y-Re alloy with various surface conditions in simulated body fluid," *Acta Biomaterialia*, vol. 5, 2009, pp. 162-171.

Hague et al. "Bioabsorption Qualities of Chitosan-absorbable Vascular Templates," *Current Surgery*, 2001, 58(1): 77-80.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Developments in metallic biodegradable stents," *Acta Biomaterialia*, 2010, 6: 1693-1697.

Hermawan et al., "Degradable metallic biomaterials: Design and development of Fe-Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, 2007, 15-17:113-118.

Hermawan et al., "Development of Degradable Fe-35Mn Alloy for Biomedical Application," *Advanced Material Research*, 2007, 15-17:107-112.

Hermawan et al., "Fe-Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, 51(1):38-45.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Hutten, A. et al. "Ferromagnetic FeCo nanoparticles for biotechnology". (2005) *Journal of Magnetism and Magnetic Materials*293:93-101).

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of of λFe2O3 nanoparticles with aminopropylsilyl groups and interparticle linkage with a, w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability received in PCT/US2007/078479, mailed Mar. 26, 2009, 8 pages.

International Search Report / Written Opinion in PCT/US09/046750 mailed Jul. 20, 2010, 14 pages.

International Search Report and Written Opinion received in PCT/US2007/078417, mailed Jan. 22, 2009, 18 pages.

International Search Report and Written Opinion received in PCT/US2007/078479, mailed Dec. 30, 2008, 12 pages.

International Search Report from PCT/US 03/20215, mailed Nov. 11, 2003, 4 pages.

International Search Report/Written Opinion in PCT/US2007/078407, mailed Mar. 26, 2008, 10 pages.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11A1-0.5Zn matrix composite," *Materials Science and Engineering A*, 2004, 381: 223-229.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kokubo et al., "How useful is SBF in predicting in vivo bone bioactivity?" *Biomaterials*, 2006, 27: 2907-2915.

LaFont, "Arterial Remodeling Technologies: Bioresorbable Stents," *Euro PCR09*, 2009, pp. 1-28.

Lee, J. et al. "Simple synthesis of mesoporous carbon with magnetic nano particles embedded in carbon rods". (2005) *Carbon* 43:2536-2543.

Lee, Sang-Yup et al. "Surface modification of magnetic nanoparticles capped by oleic acids: Characterization and collodial stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liu et al., "Characterizations of polypyrrole (PPy) nano-tubules made by templated ac electropolymerization," *European Polymer Journal*, 2005, 41: 2117-2121.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Meng Han, "Laser nitriding of metals: Influences of the ambient pressure and the pulse duration," 2001, Dissertation, Georg-August-Universität Göttingen, 134 pages.

*Methods in Cell Biology (Cell Death)*, vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niinisto, "Atomic Layer deposition: A key technology for the controlled growth of oxide thin films for advanced applications," *Proc. Estonian Acad. Sci. Phys. Math.*, 2003, 52(3):266-276.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ouerd et al., "Reactivity of Titanium in Physiolgoical Medium- I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET2006*, Jun. 2006, pp. 1-30.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine9*, (2008) pp. 248-254.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Reece et al., "Metal transport studies on inherently conducting polymer membranes containing cyclodextrin dopants," *Journal of Membrane Science*, 2005, 249: 9-20.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical Characterization of the corrosion of a magnesium rare-earth alloy in simulated body fluids," *Journal of Biomedical Materials Research Part A*, 2007, 167-175.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Schauer et al., "Protection of iron against corrosion with polyaniline primers," *Progress in Organic Coatings*, 1998, 33: 20-27.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geolgical Society of London*, p. 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shieh et al. "Aqueous dispersions of magnetite nanoparticles with NH3 surfaces for magnetic manipulations of biomolecules and MRI contrast agents" *Biomaterials*, 2005 26: 7183-7191.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Soto et al., "Amorphous magnesium nitride films produced by reactive pulsed lasar deposition," Journal of Non-Crystalline Solids, 2004, 342: 65-69.

Stoner et al., "The mechanism of low frequency a.c. Electrochemical Disinfection," *Bioelectrochemistry and Bioenergetics*, 1982, 9:229-243.

Su et al., "Photoacoustic imaging of coronary artery stents," *Optics Express*, vol. 17, No. 22, Oct. 26, 2009, pp. 1-8.

Sun et al., "Fabrication of a multilayer film electrode containing porphyrin and its application as a potentiometric sensor of iodide ion," *Talanta*, 1998, 46: 15-21.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Virtanen et al., "Electrochemical Behavior of Fe in Phosphate Solutions Studied by *In Situ* X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, No. 2-3, 2008, pp. 147-171.

Volkova, "Effect of Deformation and Heat Treatment on the Structure and Properties of Magnesium Alloys of the Mg-Zn-Zr System," *Metal Science and Heat Treatment*, vol. 48, No. 11-12, 2006, pp. 508-512.

Volynova et al., "Mechanical Properties and the Fine Structure of Powdered of Magnesium Alloys," *Plenum Publishing Corp.*, 1987, pp. 999-1006.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wan et al., "Preparation and characterization of porous conducting poly(DL-lactide) composite membranes," *Journal of Membrane Science*, 2005, 246: 193-201.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Weiss et al., "Pyrrole derivatives for electrochemical coating of metallic medical devices," *J. Polymer Science, Part A: Polymer Chemistry*, 2004, 42: 1658-1667.

White and Slade, "Polymer electrodes doped with heteropolymetallates and their use within solid-state supercapacitors," *Synthetic Metals*, 2003, 139: 123-131.

Wilcox, "Biodegradable Technology: Medtronic Biodegradable Stent Program," *Euro PCR09*, 2009, pp. 1-25.

Windecker et al., "Biolimus-eluting stent with biodegradable polymer versus sirolimus-eluting stent with durable polymer for coronary revascularisations (LEADRERS): a randomized non-inferiority trial," the *Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Ye et al., "In situ synthesis of AlN particles in Mg-Al alloy by $Mg_3$-$N_2$addition," *Materials Letters*, 2004, 58: 2361-2361.

Yen et al., "Electrochemical treatment of human KB cells in vitro," *Bioelectromagnetics*, 1999, 20:34-41.

Y fantis et al., "Novel corrosion-resistant films for Mg alloys," *Surface and Coatings Technology*, 2002, 151-152: 400-404.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}{}_{62}$doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," *Colloids and Surfaces A: Physiochem. Eng. Aspects*, 2006, 273: 16-23.

International Preliminary Report on Patentability from PCT/US08/75976 dated Mar. 25, 2010, mailed Nov. 25, 2008, 8 pages.

Deepwater, "Galvanic Series," http://corrosion-doctors.org/definitions/galvanic-series.htm> on Mar. 11, 2011 5 pages.

Wikipedia, the Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

\* cited by examiner

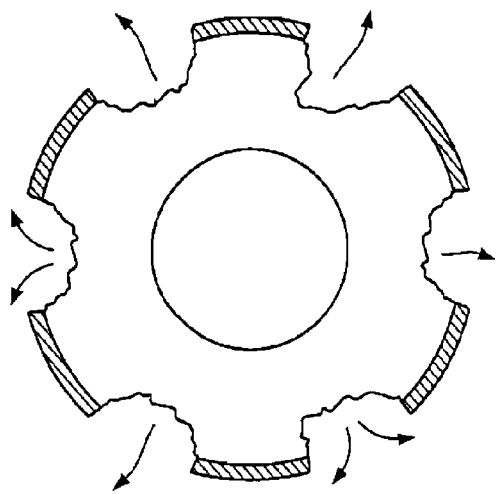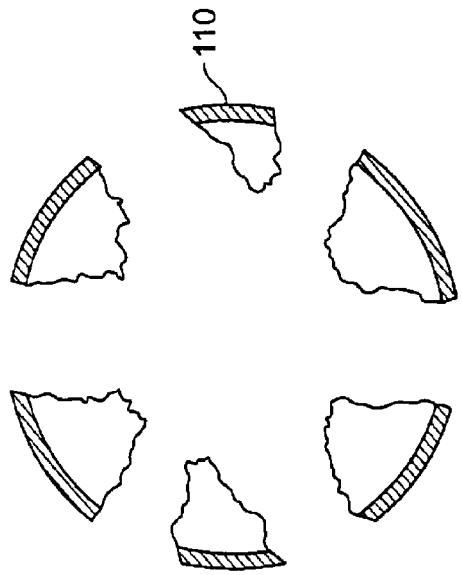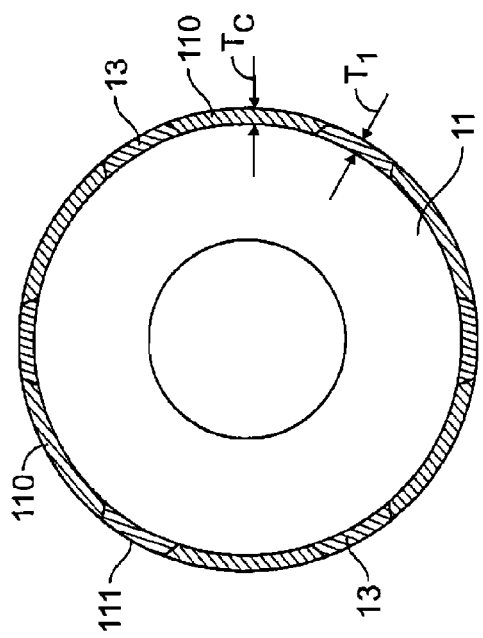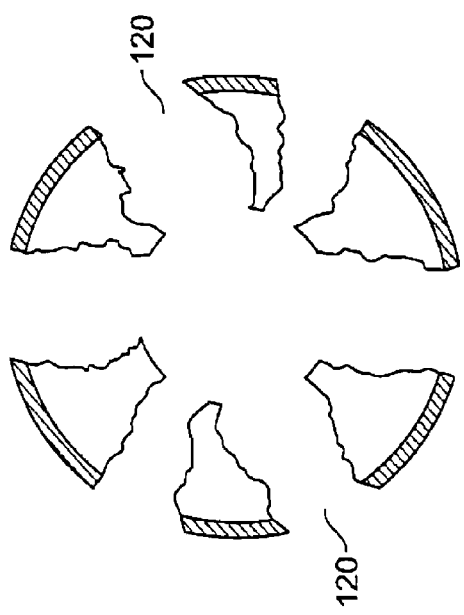

BIOERODIBLE METALLIC ENDOPROSTHESES

CROSS-REFERENCE TO RELATED APPLICATIONS

This application claims priority under 35 USC §119(e) to U.S. Provisional Patent Application Ser. No. 60/845,341, filed on Sep. 18, 2006, the entire contents of which are hereby incorporated by reference.

TECHNICAL FIELD

This disclosure relates to endoprostheses, and to methods of making and delivering the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

This disclosure generally relates to endoprostheses that are, or that include portions that are, erodible or bioerodible.

In one aspect, the disclosure features implantable endoprostheses that include a bioerodible body that includes a first bioerodible material. The bioerodible body carries a plurality of discrete, spaced apart biocrodible regions that include a second biocrodible material different from the first biocrodible material.

In embodiments, each discrete, spaced apart region extends from an outer surface of the bioerodible body. In such embodiments, a longitudinal spacing between immediately adjacent regions can be, e.g., between about 1.0 µm and about 35 µm, and/or a transverse spacing between immediately adjacent regions can be, e.g., between about 1.0 µm and about 35 µm, measured along an outer surface of the bioerodible body from which the regions extend. Also, in such embodiments, a thickness of the bioerodible body can be, e.g., from about 0.5 mm to about 5.0 mm; a thickness of each region can be, e.g., from about 0.01 µm to about 5 µm; and/or an outermost top surface of each region can have, e.g., an area of not more than about 25 µm$^2$.

In embodiments, each discrete, spaced apart region extends inwardly beyond an outermost surface of the bioerodible body. In such embodiments, a longitudinal spacing between immediately adjacent regions can be, e.g., between about 1.0 µm and about 35 µm and/or a transverse spacing between immediately adjacent regions can be, e.g., between about 1.0 µm and about 35 µm, measured along an outer surface of the bioerodible body. Also, in such embodiments, a thickness of the bioerodible body can be, e.g., from about 0.5 mm to about 5.0 mm; a thickness of each region can be, e.g., from about 0.01 µm to about 5 µm; and/or an outermost top surface of each region has an area of not more than about 25 µ$^2$.

In embodiments, the endoprosthesis further includes a coating about the endoprosthesis. If desired, the coating can, e.g., include a therapeutic agent thereon and/or therein, such as one that inhibits restenosis.

The biocrodible body can be, e.g., in the form of a tube.

The bioerodible body can include, e.g., a bioerodible metallic material, such as iron, magnesium, zinc, aluminum, calcium, or alloys thereof.

Each region can include, e.g., a bioerodible metallic material.

In embodiments, the bioerodible body and each region includes a bioerodible metal. If the metals are disparate, the biocrodible body and each region can together define a galvanic couple. In such instances, a standard cell potential for the galvanic couple can be, e.g., at least +1.0 V.

The implantable endoprosthesis can be, e.g., in the form of a stent, a stent-graft or a filter.

If desired, the biocrodible body and/or one or more of the regions can be, e.g., electrically connected to a battery. Such embodiments can, e.g., increase an overall bioerosion rate of the endoprosthesis. In such embodiments, a current of, e.g., from about 1 µA to about 250 µA can flow through a circuit that includes the bioerodible body and/or one or more of the regions and the battery.

In another aspect, the disclosure features, implantable endoprostheses that include a bioerodible body. Fragments having a maximum dimension of not more than about 25 µm are generated during erosion of the implantable endoprosthesis in Ringer's solution.

For example, the bioerodible body can include a first bioerodible material, and can carry a plurality of discrete, spaced apart bioerodible regions that include a second bioerodible material different from the first bioerodible material.

Preferably, the maximum dimension is not more than about 10 µm, not more than about 5 µm or not more than 1 µm.

In another aspect, the disclosure features implantable endoprostheses that include a bioerodible body and a coating about the bioerodible body. The coating substantially prevents fragments of the bioerodible body from detaching from the endoprosthesis during bioerosion.

In embodiments, the bioerodible body includes a metallic material, and/or the bioerodible body includes a first bioerodible material, and the bioerodible body carries a plurality of discrete, spaced apart bioerodible regions that include a second bioerodible material different from the first bioerodible material. If desired, each discrete, spaced apart region can extend from an outer surface of the bioerodible body.

In embodiments, the coating is disposed between the spaced apart regions.

In another aspect, the disclosure features methods of making implantable endoprostheses. The methods include providing a bioerodible body that includes a first bioerodible material; and forming a plurality of discrete, spaced apart bioerodible regions that includes a second bioerodible material different from the first bioerodible material. The regions are formed such that the bioerodible body carries the bioerodible regions. In some embodiments, a coating is formed on the bioerodible body.

Aspects and/or embodiments may have one or more of the following advantages. The endoprostheses can be configured to erode in a predetermined fashion and/or at a predetermined time after implantation into a subject, e.g., a human subject. For example, the predetermined manner of erosion can be from an inside of the endoprosthesis to an outside of the endoprosthesis, or from a first end of the endoprosthesis to a second end of the endoprosthesis. Many of the endoprostheses have portions which are protected from contact with bodily materials until it is desired for such portions to contact the bodily materials. The endoprostheses can exhibit a reduced likelihood of uncontrolled fragmentation. The manner of fragmentation and fragmentation size can be controlled. The endoprostheses may not need to be removed from the body after implantation. Lumens implanted with such endoprostheses can exhibit reduced restenosis. The endoprostheses can have a low thrombogenecity. Some of the endoprostheses can be configured to deliver a therapeutic agent. Some of the endoprostheses have surfaces that support cellular growth (endothelialization).

An erodible or bioerodible endoprosthesis, e.g., a stent, refers to a device, or a portion thereof, that exhibits substantial mass or density reduction or chemical transformation, after it is introduced into a patient, e.g., a human patient. Mass reduction can occur by, e.g., dissolution of the material that forms the device and/or fragmenting of the device. Chemical transformation can include oxidation/reduction, hydrolysis, substitution, electrochemical and/or addition reactions, or other chemical reactions of the material from which the device, or a portion thereof, is made. The erosion can be the result of a chemical and/or biological interaction of the device with the body environment, e.g., the body itself or body fluids, into which it is implanted and/or erosion can be triggered by applying a triggering influence, such as a chemical reactant or energy to the device, e.g., to increase a reaction rate. For example, a device, or a portion thereof, can be formed from an active metal, e.g., Mg or Ca or an alloy thereof, and which can erode by reaction with water, producing the corresponding metal oxide and hydrogen gas (a redox reaction). For example, a device, or a portion thereof can be formed from an erodible or bioerodible polymer, or an alloy or blend erodible or biocrodible polymers which can erode by hydrolysis with water. The erosion occurs to a desirable extent in a time frame that can provide a therapeutic benefit. For example, in embodiments, the device exhibits substantial mass reduction after a period of time which a function of the device, such as support of the lumen wall or drug delivery is no longer needed or desirable. In particular embodiments, the device exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the device exhibits fragmentation by erosion processes. The fragmentation occurs as, e.g., some regions of the device erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the device exhibits erodibilty. For example, an exterior layer or coating may be erodible, while an interior layer or body is non-erodible. In embodiments, the endoprosthesis is formed from an erodible material dispersed within a non-erodible material such that after erosion, the device has increased porosity by erosion of the erodible material.

Erosion rates can be measured with a test device suspended in a stream of Ringer's solution flowing at a rate of 0.2 m/second. During testing, all surfaces of the test device can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

As used herein, "metallic material" means a pure metal, a metal alloy or a metal composite.

All publications, patent applications, patents, and other references mentioned herein are incorporated by reference herein in their entirety.

Other aspects, features, and advantages will be apparent from the description and drawings, and from the claims.

DESCRIPTION OF DRAWINGS

FIG. 1A showing the stent in a collapsed state; FIG. 1B showing expansion of the stent; and FIG. 1C showing deployment of the stent.

FIGS. 3A and 3B being transverse cross-sectional views; FIGS. 3C and 3D being perspective views; and FIG. 3E being a top view.

FIG. 5 is a transverse cross-sectional view the stent of FIG. 2 having a coating that fills spaces between the discrete, spaced apart regions.

FIGS. 5A-5C is a series of transverse cross-sectional views, illustrating bioerosion of one embodiment of the stent of FIG. 5.

DETAILED DESCRIPTION

Figure 1A:
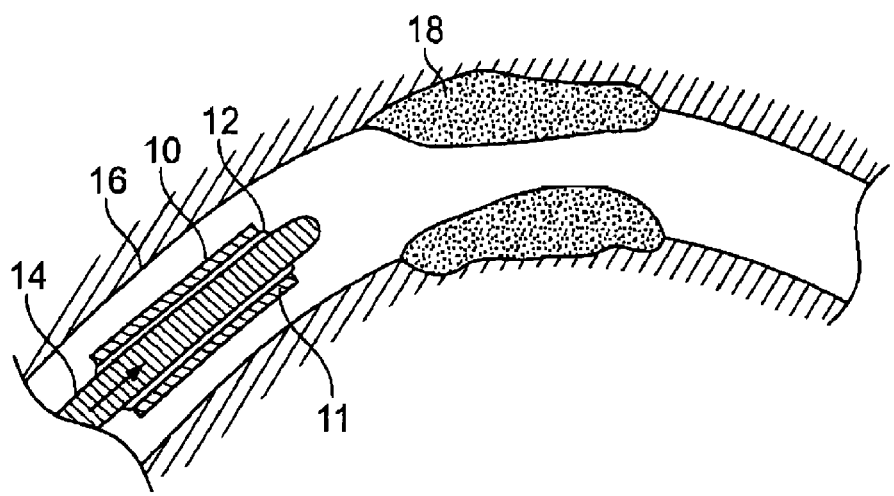
FIGS. 1A-1C are longitudinal cross-sectional views, illustrating delivery of a stent that includes a bioerodible body that carries a plurality of discrete, spaced apart bioerodible regions extending from an outer surface of the bioerodible body.
Figure 1B:
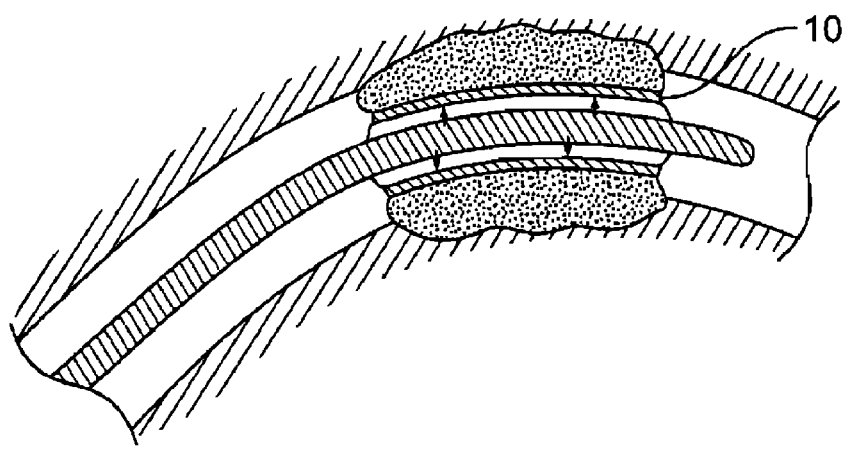
Figure 1C:
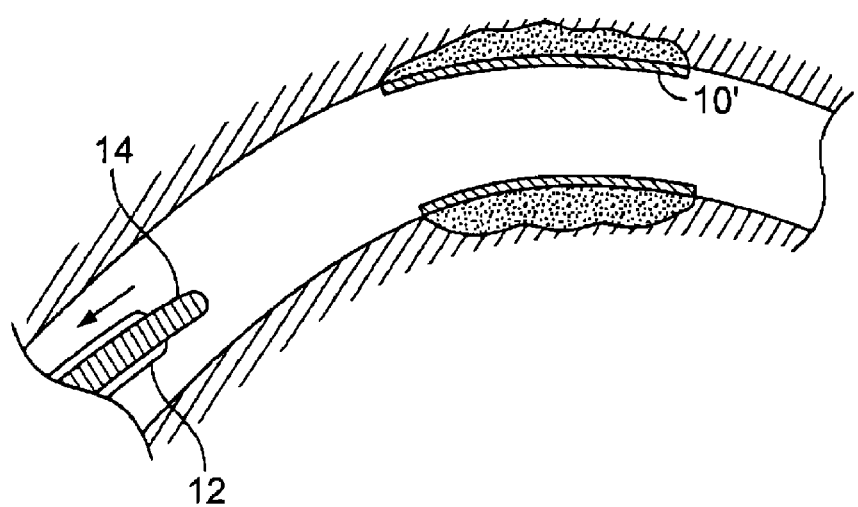

Referring to FIGS. 1A-1C and 2-2B, a stent 10 includes a tubular bioerodible body 1 that includes a first biocrodible material. The bioerodible body 11 is circular in transverse cross-section, and carries a plurality of discrete, spaced apart bioerodible regions 13 that extend outwardly from an outer surface 15 of the body 11. As shown, each region 13 defines a projection that is rectangular when viewed from above, although the regions may not be visible with a naked eye due to their size. In some instances, the regions may need to visualized with an optical microscope or scanning electron microscope. The regions 13 include a second bioerodible material that is different from the first biocrodible material. Stent 10 is placed over a balloon 12 carried near a distal end of a catheter 14, and is directed through a lumen 16 (FIG. 1A) until the portion carrying the balloon 12 and stent 10 reaches the region of an occlusion 18. The stent 10 is then radially expanded by inflating the balloon and compressed against the vessel wall with the result that occlusion is compressed, and the vessel wall surrounding it undergoes a radial expansion (FIG. 1B). The pressure is then released from the balloon 12 and the catheter 14 is withdrawn from the vessel (FIG. 1C), leaving behind the expanded stent 10' in lumen 16.

The material from which the regions 13 are formed, the thickness $T_1$ of the regions, the material from which the bioerodible body 11 is formed, the thickness T of the body, the transverse spacing $S_T$ between regions and the longitudinal spacing $S_l$ between regions are chosen to provide the desired mechanical properties, along with a desired bioerosion rate, manner of bioerosion and fragmentation size, e.g., not more than about 25 μ. In embodiments, the fragments have a maximum dimension of not more than about the size of a large white blood cell, e.g., not more than about 15 μm. In preferred embodiments, the maximum dimension is not more than about 10 μm, not more than about 5 μm, or not more than about 1 μm.

Figure 2:
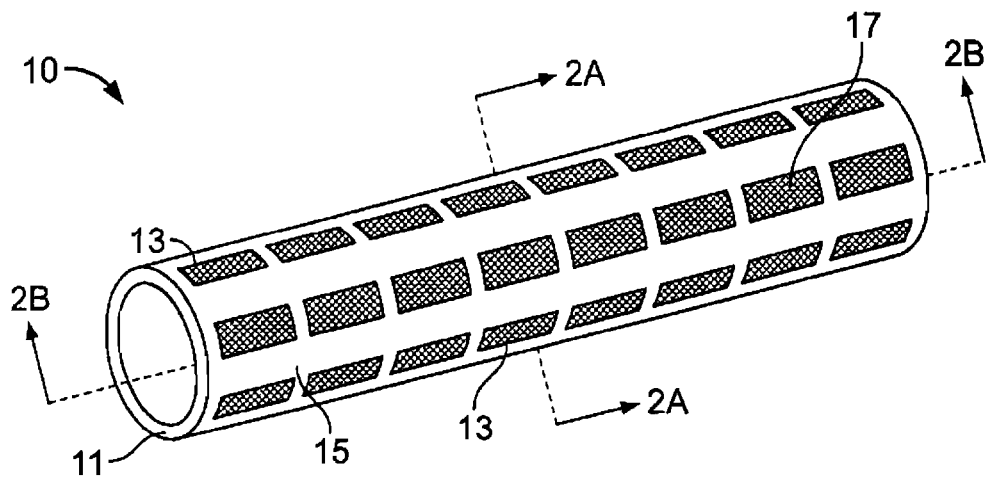
FIG. 2 is a perspective view of the unexpanded stent of FIG. 1A.
Figure 2A:
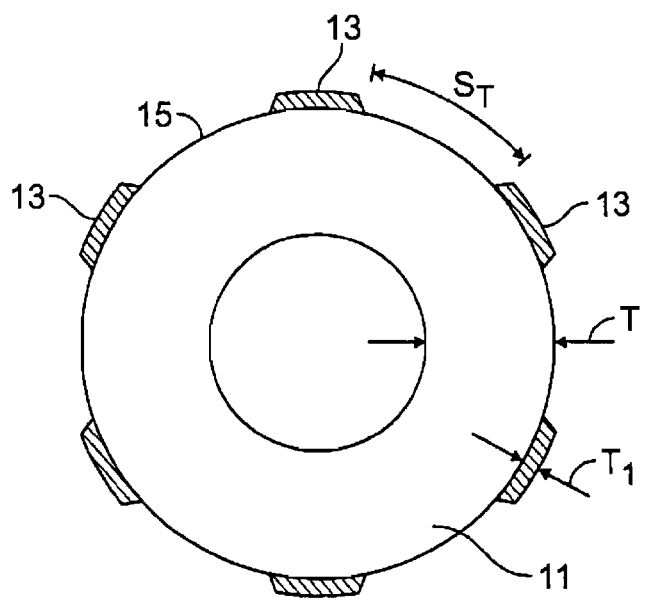
FIG. 2A is a transverse cross-sectional view of the stent of FIG. 2, taken along 2A-2A.
Figure 2B:
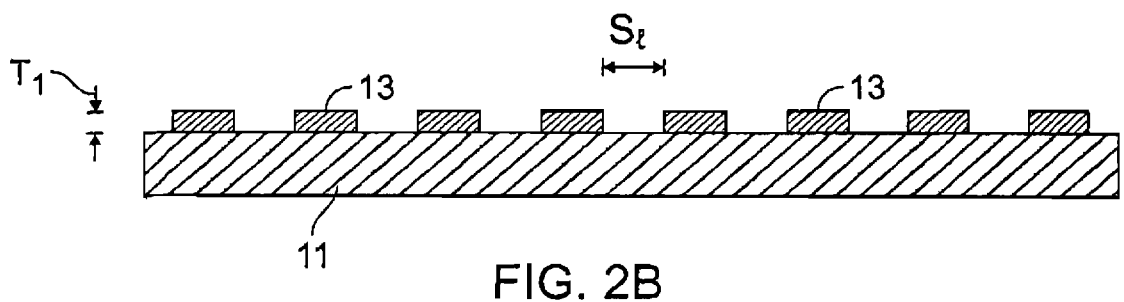
FIG. 2B is a longitudinal cross-sectional view of the stent of FIG. 2, taken along 2B-2B.
Figure 3A:
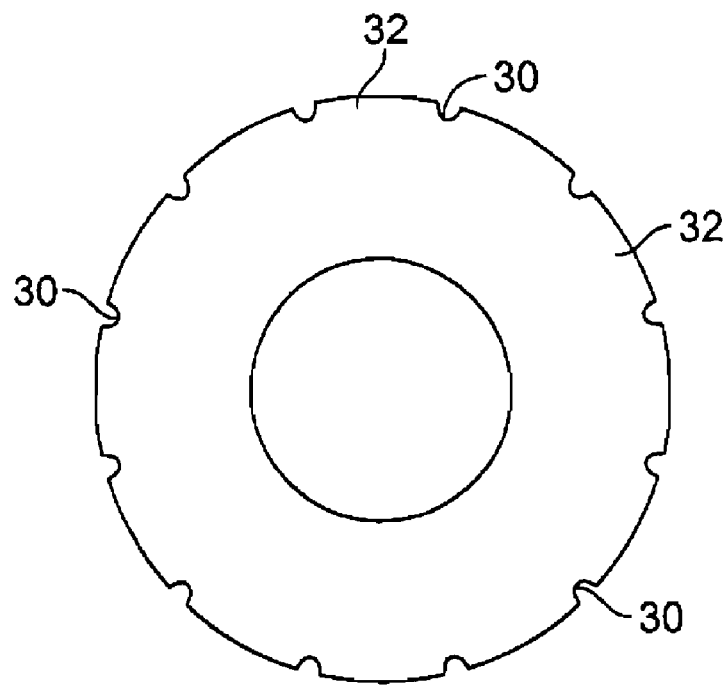
FIGS. 3A-3E illustrate bioerosion of one embodiment of the stent of FIG. 2.
Figure 3B:
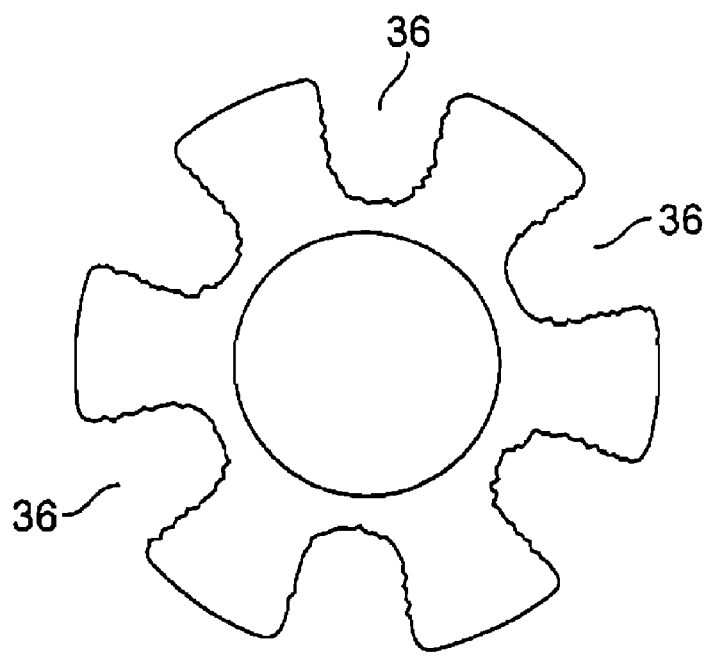
Figure 3C:
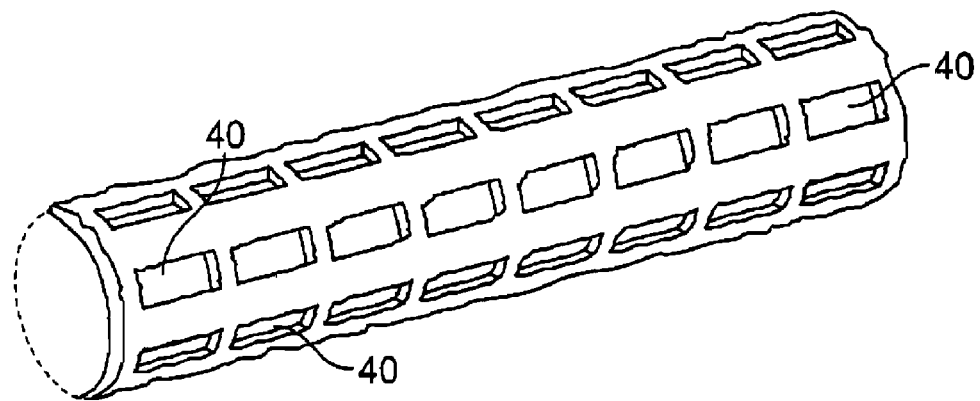
Figure 3D:
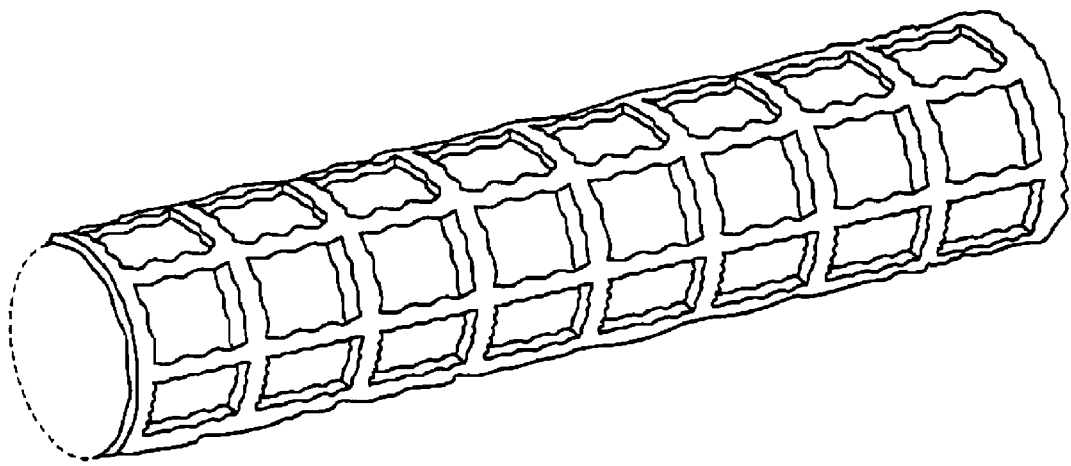
Figure 3E:
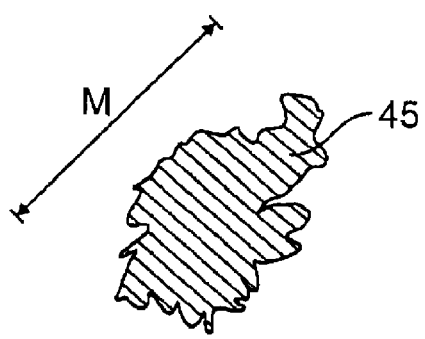

Referring as well now to FIGS. 3A-3E, which illustrate bioerosion of one embodiment of the stent shown in FIG. 2 in which body 11 is formed of, e.g., iron and regions 13 are formed of, e.g., magnesium. In the initial stages of bioerosion (FIG. 3A), the regions formed of magnesium erode relatively quickly, their rate of erosion being enhanced by the galvanic reaction between the iron of the body and the magnesium. In these initial stages of bioerosion, crevices 30 appear in the body proximate the regions, and portions 32 just below the regions are weakened due to the galvanic reaction. The crevices 30 enhance the rate of erosion of the iron body, it is believed, because the concentration of reactive ions in the crevices is higher, giving higher reaction rates. As bioerosion continues (FIG. 3B), deep pits 36 are formed in the iron body. Erosion in the pits is enhanced, so that the pits become apertures 40 defined in the iron body (FIG. 3C). The size of the apertures enlarge (FIG. 3D), until the body disintegrates into fragments 45 (FIG. 3E) having a maximum dimension M, e.g., not more than 15 μm, 10 μm, 5 μm, or not more than 1 μm.

In embodiments, the transverse $S_T$ spacing between immediately adjacent regions, measured along the outer surface 15 of the bioerodible body 11 is between about 1.0 μm and about 35 μm, e.g., between about 1.0 μm and about 20 μm or between about 2.0 μm and about 15 μm; and the longitudinal spacing $S_T$ between immediately adjacent regions is between about 1.0 μm and about 35 μm, e.g., between about 1.0 μm and about 20 μm or between about 2.0 μm and about 15 μm. In embodiments, an outermost top surface 17 (FIG. 2) of each region has an area not more than about 25 μm$^2$, e.g., not more than about 15 μm$^2$, or not more than about 5 μm$^2$. In embodiments, the regions 13 are formed of a biocrodible metallic material or ceramic material, and thickness $T_1$ of the regions is, e.g., between about 0.01 μm and about 10 μm, e.g., between about 0.05 μm and about 7.5 μm, or between about 0.1 μm and about 5 μm. In embodiments, the bioerodible body 11 is formed from a bioerodible metallic material or ceramic material, the transverse thickness T is, e.g., between about 0.1 mm and about 2.5 mm, e.g., between about 0.25 mm and about 2.0 mm, or between about 0.3 mm and about 1.5 mm.

In embodiments, the regions 13 and body 11 are formed of substantially disparate metals having substantially different standard reduction potentials, setting up a galvanic reaction between the disparate metals. For example, a standard cell potential for the galvanic couple can be greater than about 2.00 V, e.g., greater than 1.75 V, 1.50 V, 1.00 V, 0.5 V, or greater than about 0.25 V. In such instances, one of the metals enhances the erosion of the other metal; while, at the same time, the other metal is protected from erosion by the other metal. For example, in a particular embodiment, the body is formed of iron and each region is formed of magnesium. In this instance, the erosion of magnesium is enhanced by the iron; while, at the same time, the erosion of iron is suppressed. Such a stent configuration can reduce overall degradation time of the entire stent and/or enhance control of where degradation starts along the stent. Erosion of magnesium and magnesium alloys is reviewed by Ferrando in *J. Mater. Eng.*, 11, 299 (1989). If desired, the biocrodible body and/or one or more of the regions can be electrically connected to a battery, e.g., to enhance the erosion rate of the stent or a portion of the stent. For example, a current of from about 1 μA to about 250 μA, e.g., from about 5 μA to about 175 μA or from about 10 μA to about 100 μA can flow through a circuit that includes the bioerodible body and/or one or more of the regions and the battery.

In embodiments, body 11 is formed of a material that has a lower bioerosion rate than regions 13. For example, the material of the body can erode at rate that is, e.g., less than about 50 percent of the rate of erosion of the material of the regions, less than about 35 percent, less than about 20 percent, less than about 15 percent, less than about 10 percent, less than about 5 percent, less than about 2.5 percent, or even less than about 1 percent of the rate of erosion of the material of the regions. For example, in a particular embodiment, body 11 is formed of iron and regions 13 are formed of magnesium, e.g., deposited by sputtering on the outer surface 15 of the bioerodible body 11. A stent can be tested by suspending the stent in a stream of Ringer's solution flowing at a rate of 0.2 m/second at 25° C., and measuring the fragments formed during erosion. The number and size of the fragments can be determined using laser light scattering. For the purposes of this disclosure, Ringer's solution is a solution of recently boiled distilled water containing 8.6 gram sodium chloride, 0.3 gram potassium chloride, and 0.33 gram calcium chloride per liter.

The regions 13 can be made by a variety of techniques including dip coating, spray coating, pulsed laser deposition, physical vapor deposition (e.g., sputtering), chemical vapor deposition, vacuum arc deposition, electrochemical plating, powder coating, painting, electro-coating, sol-gel coating and polymer plating (e.g., plasma polymerization). Pulsed laser deposition is described by Wang et al. in *Thin Solid Films*, 471, 86-90 (2005); vacuum arc deposition is described by Straumal et al. in *Thin Solid Films*, 383, 224-226 (2001); sputtering is described by Gopalraja et al. in U.S. Pat. No. 6,991,709; coatings on magnesium are reviewed by Gray et al. in *Journal of Alloys and Compounds*, 336, 88-113 (2002).

Figure 4:
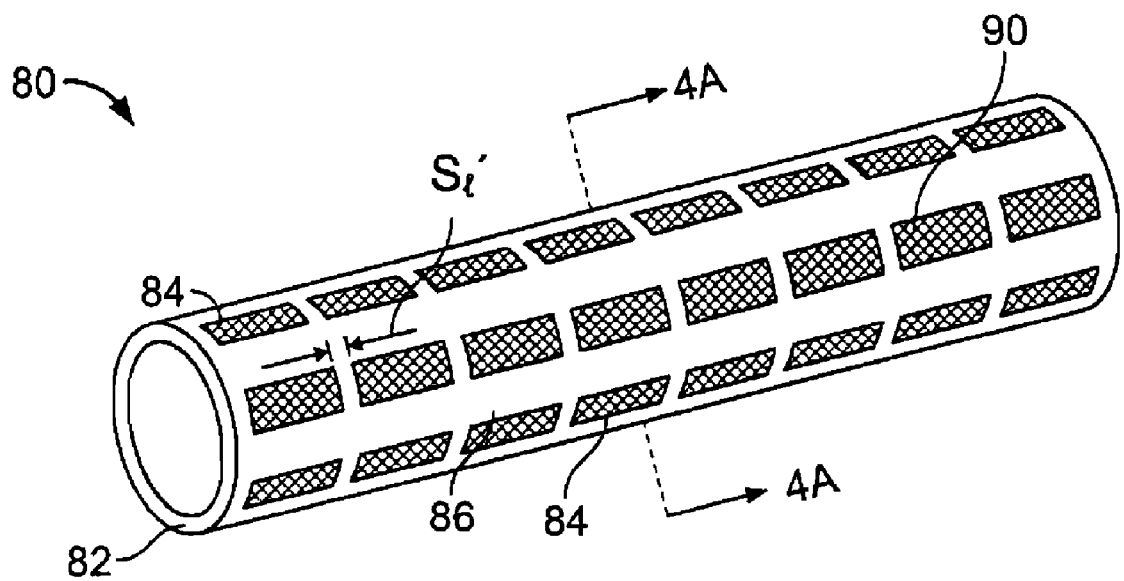
FIG. 4 is a perspective view of an alternative embodiment of a stent that includes a biocrodible body that carries a plurality of discrete, spaced apart bioerodible regions that extend inwardly beyond an outermost surface of the bioerodible body.
Figure 4A:
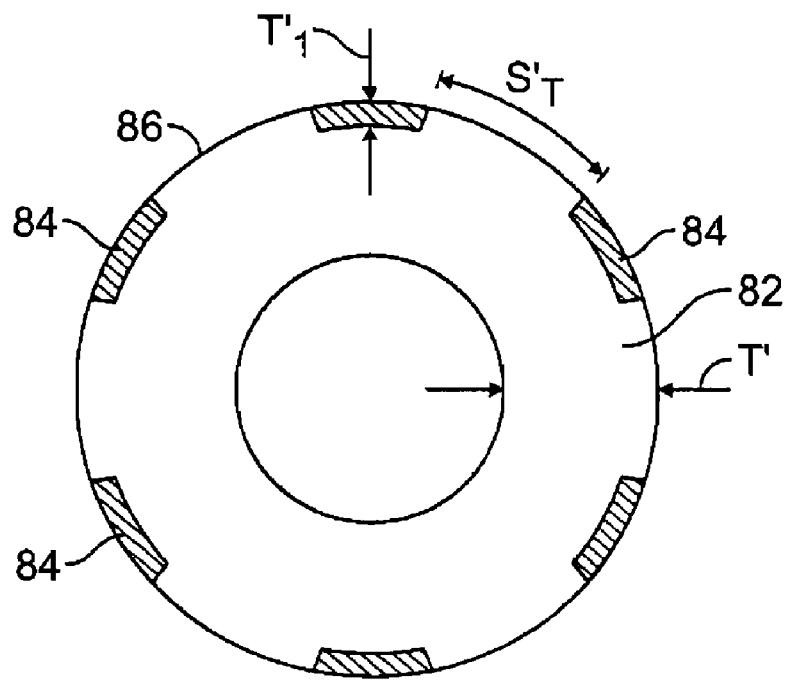
FIG. 4A is a transverse cross-sectional view of the stent of FIG. 4, taken along 4A-4A.

Referring now to FIG. 4 and 4A, in an embodiment, a stent 80 includes a tubular bioerodible body 82 that includes a first bioerodible material. The bioerodible body 82 is circular in transverse cross-section, and carries a plurality of discrete, spaced apart bioerodible regions 84 that extend inwardly beyond an outer surface 86 of the bioerodible body 82. As shown, each region 84 is rectangular when viewed from above and forms a smooth transition on its edges with the outer surface 86 of the bioerodible body 82. The regions may not be visible with a naked eye due to their size or due to small visual differences between the body material and the material of the regions. In some instances, the regions may need to visualized with an optical microscope of scanning electron microscope. The regions 84 include a second bioerodible material that is different from the first bioerodible material. Stent 80 can be delivered as discussed above in reference to the stent of FIG. 2.

In embodiments, the regions 84 and body 82 are formed of substantially disparate metals having substantially different standard reduction potentials, setting up a galvanic reaction between the disparate metals. For example, body 82 can be formed of iron and regions 84 can be formed of magnesium or a magnesium alloy. As discussed above, the bioerodible body and/or one or more of the regions can be electrically connected to a battery, e.g., to enhance the erosion rate of the stent or a portion of the stent. Thickness $T_t'$, the material from which the bioerodible body 82 is formed, the thickness T', the spacing $S_T'$ and spacing $S_l'$ can have any of the values discussed above in reference to the stent of FIG. 2. An outermost top surface 90 of each region can, e.g., have an area of not more than about 25 $\mu m^2$, e.g., not more than about 15 $\mu m^2$, or not more than about 5 $\mu m^2$.

The regions can be formed by etching apertures into the stent body and filling the apertures with a second bioerodible material. The regions 84 can be made by techniques including ion implantation (e.g., plasma immersion ion implantation) in which the stent body is modified in discrete regions, laser treatment and chemical treatment. Plasma immersion ion implantation (PIII) is described by Weber et al. in "Medical Balloons And Methods Of Making The Same", U.S. patent application Ser. No. 11/355,392, filed Feb. 16, 2006, and "Bioerodible Endoprostheses And Methods Of Making The Same", U.S. patent application Ser. No. 11/355,368, filed Feb. 16, 2006; by Chu in U.S. Pat. No. 6,120,660; and by Brukner and Kutsenko in *Acta Materialia*, 52, 4329-4335 (2004).

Referring now to FIG. 5, in one embodiment, the stent of FIG. 2 can include a coating 110 that fills the spacing between regions 13, but does not cover the regions 13. In the particular embodiment shown, the thickness $T_c$ of the coating is such that is does not extend beyond the thickness $T_1$ of the regions 13. Coating 110 can be bioerodible or non-bioerodible. When the coating 110 is non-bioerodible, it can be or can include a polymeric material, a metallic material (e.g., a metal or metal alloy) or a ceramic material.

Referring as well now to FIGS. 5A-5C, in a particular embodiment, the body 11 is iron, regions 13 are formed of magnesium and coating 110 is a non-bioerodible, the coating prevents direct contact between the material that forms biocrodible body 11 and the lumen in which the stent is implanted, and also allows for additional control on how the stent bioerodes. In the initial stages of bioerosion (FIG. 5A), the regions formed of magnesium and portions in close proximity under the regions erode relatively quickly, their rate of erosion being enhanced by the galvanic reaction between the iron of the body and the magnesium. As bioerosion continues, deep pits become apertures 120 that do not grow in size externally because of coating 110 prevents bioerosion of the bioerodible material of the body directly underneath (FIG. 5B). Bioerosion then proceeds from the inside toward the outside, the coating 110 acting as "glue" to keep the stent from fragmenting within the lumen.

Figure 6:
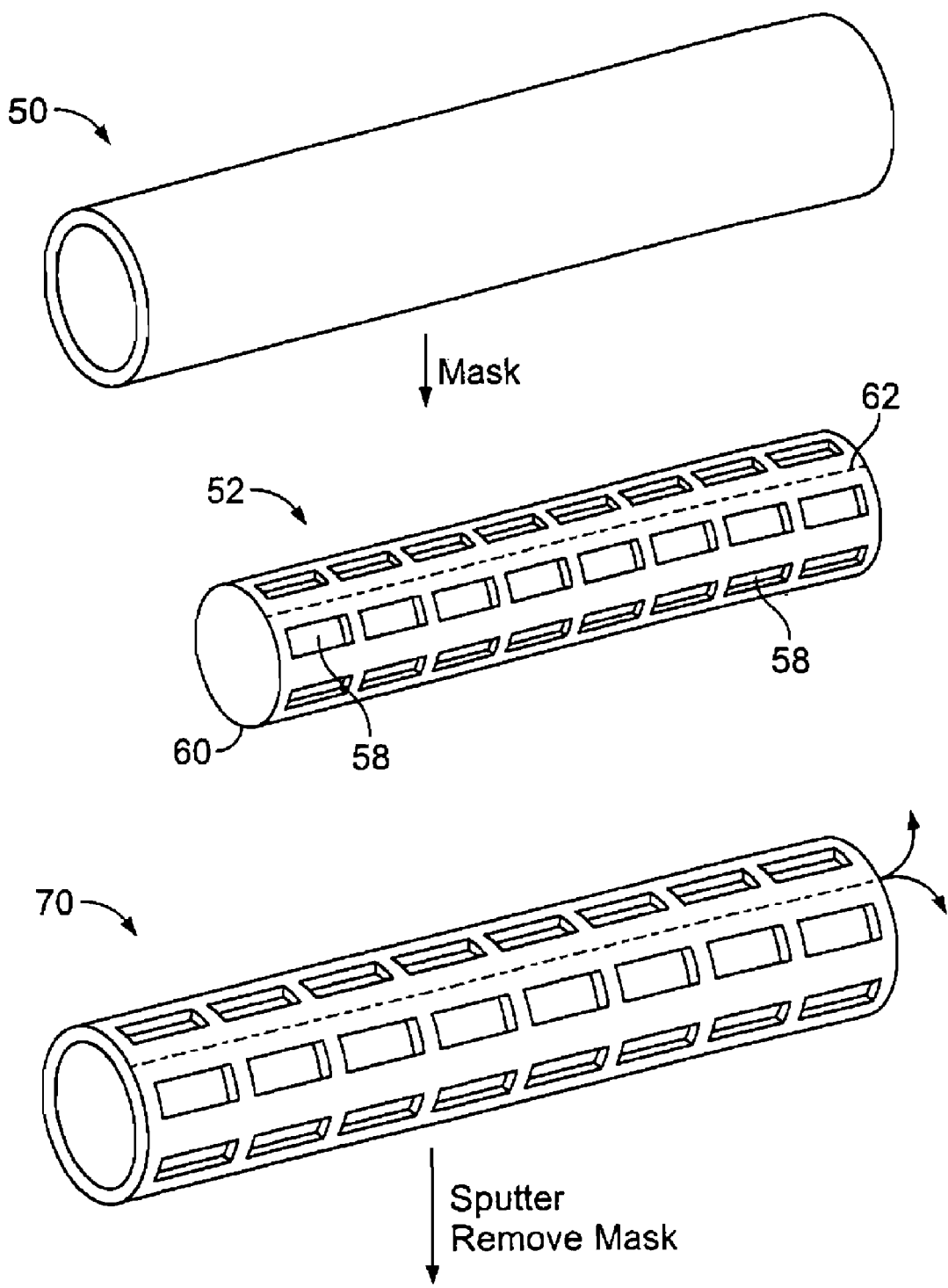
FIG. 6 is a series of perspective views, showing one method of manufacturing a stent.

Referring now to FIG. 6, a stent can be made by providing a hollow tubular pre-stent 50, and then placing a mask 52 about the pre-stent 50. Mask 52 can be made of a thin sheet material, such as MYLAR® polyester film or heat-shrinkable polyolefin film, having a thickness approximately equal to thickness $T_1$ of regions 13. Mask 52 has a plurality of apertures 58 defined in a wall 60 of the mask that correspond dimensionally to regions 13. In addition, mask 52 includes a perforation 62 so that is can be removed after regions 13 are formed. The apertures and perforations can be formed by lithography, laser ablation or cutting. Regions can be formed by the techniques described above. For example, material can be sputtered on assembly 70 while rotating the assembly. Sputtered material can contact the pre-stent through the apertures, but is prevented from contacting the pre-stent in the masked areas. After regions are formed, mask 52 is removed by tearing along the perforation 62 to release the stent.

As described above, regions can be patterned on a stent that increase the rate of erosion. In embodiments regions can be patterned on a stent that decrease the rate of erosion. For example, an erodible or nonerodible metal, ceramic, or polymer coating is provided on a stent that protects portions of the stent from exposure to body fluids or galvanic corrosions while exposing other portions where that erosion proceeds. The coating can be a polymer or a material that is erodible or nonerodible. Coatings can be provided on only the exterior, only on the interior or on both the exterior and the interior or the stent.

In embodiments the bioerodible body is formed from a bioerodible polymeric material, the transverse thickness T can be, e.g., between about 0.5 mm and about 5.0 mm, e.g., between about 0.5 mm and about 3.0 mm, or between about 1 mm and about 2.5 mm. In embodiments in which the regions are formed of a bioerodible polymeric material, the thickness $T_1$ of the regions can be, e.g., between about 1 μm and about 100 μm, e.g., between about 1 μm and about 50 μm, or between about 5 μm and about 35 μm.

Various bioerodible materials, polymers and ceramics can be used in the embodiments described herein.

Example of bioerodible metals or a metal alloys from which the regions 13 can be formed include iron and magnesium. Examples of iron alloys include low-carbon steel (AISI 1018-1025), medium carbon steel (AISI 1030-1055), high carbon steel (1060-1095), and binary Bi—Fe alloys. Other examples of alloys include magnesium alloys, such as, by weight, 50-98% magnesium, 0-40% lithium, 0-5% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2-4% aluminum and 1-2% rare earths; or 8.5-9.5% aluminum, 0.15-0.4% manganese, 0.45-0.9% zinc and the remainder magnesium; or 4.5-5.3% aluminum, 0.28-0.5% manganese and the remainder magnesium; or 55-65% magnesium, 30-40% lithium and 0-5% other metals and/or rare earths. Magnesium alloys are available under the names AZ91D, AM50A, and AE42, which are available from Magnesium-Elektron Corporation (United Kingdom). Other erodible metals or metal alloys are described by Bolz in U.S. Pat. No. 6,287,332 (e.g., zinc-titanium alloy and sodium-magnesium alloys); Heublein in U.S. Patent Application 2002/0004060; Kaese in Published U.S. Patent Application No. 2003/0221307; Stroganov in U.S. Pat. No. 3,687,135; and Park in *Science and Technology of Advanced Materials*, 2, 73-78 (2001).

Examples of bioerodible ceramics from which the regions 13 can be formed include beta-tertiary calcium phosphate (β-TCP), blends of β-TCP and hydroxy apatite, $CaHPO_4$, $CaHPO_4 \cdot 2H_2O$, $CaCO_3$ and $CaMg(CO_3)_2$. Other bioerodible ceramics are discussed by Zimmermann in U.S. Pat. No. 6,908,506, and Lee in U.S. Pat. No. 6,953,594.

Examples of bioerodible polymers from which the regions 13 can be formed include polycaprolactone (PCL), polycaprolactone-polylactide copolymer (e.g., polycaprolactone-polylactide random copolymer), polycaprolactone-polyglycolide copolymer (e.g., polycaprolactone-polyglycolide random copolymer), polycaprolactone-polylactide-polyglycolide copolymer (e.g., polycaprolactone-polylactide-polyglycolide random copolymer), polylactide, polycaprolactone-poly(β-hydroxybutyric acid) copolymer (e.g., polycaprolactone-poly(β-hydroxybutyric acid) random copolymer) poly(β-hydroxybutyric acid) and mixtures of these polymers. Additional examples of biocrodible polymers are described by Sahatjian et. al. in U.S. Published Patent Application No. 2005/0251249.

Examples of non-biocrodible polymers from which the coating 110 can be formed include polycyclooctene (PCO), styrene-butadiene rubber, polyvinyl acetate, polyvinylidine-fluoride (PVDF), polymethylmethacrylate (PMMA), polyurethanes, polyethylene, polyvinyl chloride (PVC), and blends thereof. Additional examples of non-bioerodible polymers are described by Sahatjian et. al. in U.S. Published Patent Application No. 2005/0251249. Examples of non-erodible metals and metal alloys from which the coating 110 can be formed include stainless steel, rhenium, molybdenum and molybdenum-rhenium alloy. Examples of non-bioerodible ceramics from which the coating 110 can be formed include oxides of silicon (e.g., silicon dioxide), oxides of titanium (e.g., titanium dioxide) or oxides of zirconium (e.g., zirconium dioxide).

If desired, the any of the stents described herein can include a therapeutic agent on or in the stent and/or a coating about the stent. The therapeutic agent can be a genetic therapeutic agent, a non-genetic therapeutic agent, or cells. Therapeutic agents can be used singularly, or in combination. Therapeutic agents can be, e.g., nonionic, or they may be anionic and/or cationic in nature. A preferred therapeutic agent is one that inhibits restenosis. A specific example of one such therapeutic agent that inhibits restenosis is paclitaxel or derivatives thereof, e.g., docetaxel. Soluble paclitaxel derivatives can be made by tethering solubilizing moieties off the 2' hydroxyl group of paclitaxel, such as —COCH$_2$CH$_2$CONHCH$_2$CH$_2$(OCH$_2$)$_n$OCH$_3$ (n being, e.g., 1 to about 100 or more). Li et al., U.S. Pat. No. 6,730,699 describes additional water soluble derivatives of paclitaxel.

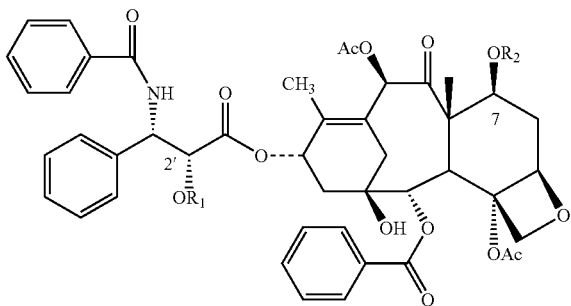

Paclitaxel: R1 = R2 = H

Exemplary non-genetic therapeutic agents include: (a) anti-thrombotic agents such as heparin, heparin derivatives, urokinase, PPack (dextrophenylalanine proline arginine chloromethylketone), and tyrosine; (b) anti-inflammatory agents, including non-steroidal anti-inflammatory agents (NSAID), such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, rapamycin (sirolimus), biolimus, tacrolimus, everolimus, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, (r) hormones; and (s) antispasmodic agents, such as alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diusopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, tropenzile, trospium chloride, xenytropium bromide, ketorolac, and pharmaceutically acceptable salts thereof.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUTPRATEK), lipids such as cationic lipids, liposomes, lipoplexes, nanoparticles, or micro particles, with and without targeting sequences such as the protein transduction domain (PTD).

Cells for use include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Any of the metallic materials, ceramic materials, or polymeric materials used to form the stent bodies, regions or coatings can be made porous. For example, a porous metal material can be made by sintering metal particles, e.g., having diameters between about 0.01 micron and about 20 micron, to form a porous material having small (e.g., from about 0.05 to about 0.5 micron) and large (e.g., from about 1 micron to about 10 micron) interconnected voids though which a fluid may flow. The voids in the porous material can be, e.g., used as depositories for a therapeutic agent that has been intercalated into the porous material or to increase erosion rate to that portion or component.

Such porous materials can have a total porosity, as measured using mercury porosimetry, of from about 80 to about 99 percent, e.g., from about 80 to about 95 percent or from about 85 to about 92 percent, and a specific surface area, as measured using BET (Brunauer, Emmet and Teller), of from about 200 $cm^2/cm^3$ to about 10,000 $cm^2/cm^3$, e.g., from about 250 $cm^2/cm^3$ to about 5,000 $cm^2/m^3$ or from about 400 $cm^2/cm^3$ to about 1,000 $cm^2/cm^3$. When bioerodible materials are utilized, the porous nature of the material can aid in the erosion of the material, as least in part, due to its increased surface area. In addition, when biocrodible materials are utilized, the porosity of the materials can ensure small fragment sizes. Porous materials and methods of making porous materials are described by Date et al. in U.S. Pat. No. 6,964,817; by Hoshino et al. in U.S. Pat. No. 6,117,592; and by Sterzel et al. in U.S. Pat. No. 5,976,454.

The stents described herein can be delivered to a desired site in the body by a number of catheter delivery systems, such as a balloon catheter system, as described above. Exemplary catheter systems are described in U.S. Pat. Nos. 5,195,969, 5,270,086, and 6,726,712. The Radius® and Symbiot® systems, available from Boston Scientific Scimed, Maple Grove, Minn., also exemplify catheter delivery systems.

The stents described herein can be configured for vascular or non-vascular lumens. For example, they can be configured for use in the esophagus or the prostate. Other lumens include biliary lumens, hepatic lumens, pancreatic lumens, uretheral lumens and ureteral lumens.

Any stent described herein can be dyed or rendered radio-opaque by addition of, e.g., radio-opaque materials such as barium sulfate, platinum or gold, or by coating with a radio-opaque material.

Any of the stents described herein or any portion of any stent described herein can be coated with a bioerodible material or a non-bioerodible material. For example, the coating can be used to deliver a drug, to protect a portion of the stent, to reduce uncontrolled fragmentation and/or to prevent contact between the stent or a portion of a stent and a portion of a lumen.

OTHER EMBODIMENTS

A number of embodiments of have been described. Nevertheless, it will be understood that various modifications may be made without departing from the spirit and scope of the disclosure.

While stents have been shown, other endoprostheses are possible. For example, the endoprothesis can be in the form of a stent-graft or a filter.

While embodiments have been shown in which the bioerodible body is in the form of a tube that is circular in cross-section when viewed end-on along the longitudinal axis of the stent (e.g., FIG. 2), the tube can have a non-circular cross-section. For example, the tube can be square, rectangular, hexagonal, or octagonal when viewed end-on along the longitudinal axis of the stent.

While embodiments have been shown in which the bioerodible regions extend from an outer surface of the bioerodible body, and embodiments have been shown in which the regions extend inwardly beyond an outer surface of the bioerodible body, in some embodiments, the regions extend both inwardly beyond and outwardly from an outer surface of the bioerodible body.

While bioerodible regions have been shown that have sharp boundaries, in some embodiments, the boundaries are more diffuse, such as would be expected using Pill.

While biocrodible regions and bodies have been shown that include a single material, in some embodiments, they include multiple materials, e.g., blends or mixtures of materials or layers of different materials.

Referring back now to FIG. 5, in addition to coating 110, the stent can include another coating disposed between the outer surface of the uncoated stent and coating 110. This other coating is, or includes, a chelating agent. For example, the other coating can be a polymeric coating that includes the chelating agent dispersed therein. The chelating agent can, e.g., chelate any metal ions generated from degradation of the stent body, preventing them from interfering with the release of the therapeutic agent from coating 110 because, e.g., the chelates are either too large to diffuse into coating 110, or they are too insoluble to diffuse into the coating. Examples of chelating agents include sodium salts of fatty acids (e.g., common soap), EDTA and porphyrins.

Still other embodiments are within the scope of the following claims.

What is claimed is:
1. An implantable endoprosthesis comprising:
    a bioerodible body comprising a first bioerodible metallic material, the bioerodible body having a thickness of between about 0.5 mm and about 5.0 mm; and
    a plurality of discrete, spaced apart bioerodible deposits comprising a second bioerodible metallic material dif- ferent from the first bioerodible metallic material, said deposits of the second bioerodible metallic material overlying the first bioerodible metallic material at a plurality of regions, each deposit having a thickness of between about 0.01 μm to about 5 μm; each region having a surface area of not more than about 25 μm², wherein the second bioerodible metallic material forms a continuous interface with the first bioerodible metallic material over the entirety of each region;

wherein a longitudinal spacing between immediately adjacent deposits is between about 1.0 μm and about 35 μm;

wherein a transverse spacing between immediately adjacent deposits is between about 1.0 μm and about 35 μm, measured along an outer surface of the bioerodible body from which the deposits extend;

wherein, when implanted within a body lumen, the bioerodible body and each deposit together define a galvanic couple that enhances a rate of erosion of the discrete, spaced apart bioerodible deposits, and wherein a standard cell potential for the galvanic couple is at least +1.0 V;

wherein erosion of the discrete, spaced apart bioerodible deposits creates crevices in the bioerodible body proximate the discrete, spaced apart bioerodible deposits, and wherein the crevices in the bioerodible body have an enhanced rate of erosion resulting in the body disintegrating into fragments having a maximum dimension of not more than 15 μm.

2. The implantable endoprosthesis of claim 1, further comprising a coating about the endoprosthesis.

3. The implantable endoprosthesis of claim 2, wherein the coating fills only spaces between the discrete, spaced apart deposits.

4. The implantable endoprosthesis of claim 2, wherein the coating comprises a therapeutic agent.

5. The implantable endoprosthesis of claim 4, wherein the therapeutic agent inhibits restenosis.

6. The implantable endoprosthesis of claim 1, wherein each of the bioerodible metallic materials is selected from the group consisting of iron, magnesium, zinc, aluminum, calcium, and alloys thereof.

7. The implantable endoprosthesis of claim 1, wherein the implantable endoprosthesis is in the form of a stent.

8. The implantable endoprosthesis of claim 1, wherein the fragments have a maximum dimension of not more than 5 μm.

* * * * *

UNITED STATES PATENT AND TRADEMARK OFFICE
CERTIFICATE OF CORRECTION

| | | |
|---|---|---|
| PATENT NO. | : 8,002,821 B2 | Page 1 of 1 |
| APPLICATION NO. | : 11/854991 | |
| DATED | : August 23, 2011 | |
| INVENTOR(S) | : Jonathan S. Stinson | |

It is certified that error appears in the above-identified patent and that said Letters Patent is hereby corrected as shown below:

1.) Title Page, Section (54) - Title: delete "ENDOPROSTHESES" and insert --ENDOPROSTHESIS--.

2.) Column 1, Line 2: delete "ENDOPROSTHESES" and insert --ENDOPROSTHESIS--.

Signed and Sealed this
Eighteenth Day of October, 2011

David J. Kappos
*Director of the United States Patent and Trademark Office*